(12) United States Patent
Gough et al.

(10) Patent No.: US 8,597,899 B2
(45) Date of Patent: *Dec. 3, 2013

(54) METHOD FOR AUTOMATED TISSUE ANALYSIS

(75) Inventors: Albert H. Gough, Glenshaw, PA (US); Kenneth A. Giuliano, Pittsburgh, PA (US); D. Lansing Taylor, Pittsburgh, PA (US)

(73) Assignee: Cernostics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,663

(22) Filed: Aug. 24, 2012

(65) Prior Publication Data

US 2013/0190198 A1 Jul. 25, 2013

Related U.S. Application Data

(63) Continuation of application No. 13/346,920, filed on Jan. 10, 2012, now abandoned, which is a continuation of application No. 12/227,334, filed as application No. PCT/US2007/011865 on May 17, 2007, now Pat. No. 8,114,615.

(60) Provisional application No. 60/801,035, filed on May 17, 2006.

(51) Int. Cl.
*G01N 31/00* (2006.01)
*G01N 33/53* (2006.01)

(52) U.S. Cl.
USPC ........... 435/7.21; 435/7.1; 436/501; 436/518; 530/300; 530/350; 424/130.1; 424/9.1

(58) Field of Classification Search
None
See application file for complete search history.

(56) References Cited

U.S. PATENT DOCUMENTS

| | | | |
|---|---|---|---|
| 5,047,321 A | 9/1991 | Loken et al. | |
| 5,733,721 A | 3/1998 | Hemstreet, III et al. | |
| 5,741,648 A | 4/1998 | Hemstreet, III et al. | |
| 5,876,946 A | 3/1999 | Burbaum et al. | |
| 5,885,840 A | 3/1999 | Kamentsky et al. | |
| 5,965,352 A | 10/1999 | Stoughton et al. | |
| 5,981,180 A | 11/1999 | Chandler et al. | |
| 5,989,835 A | 11/1999 | Dunlay et al. | |
| 6,103,479 A | 8/2000 | Taylor | |
| 6,140,048 A | 10/2000 | Muller et al. | |
| 6,203,987 B1 | 3/2001 | Friend et al. | |
| 6,204,068 B1 | 3/2001 | Soini et al. | |
| 6,218,122 B1 | 4/2001 | Friend et al. | |
| 6,242,205 B1 | 6/2001 | Dohlman et al. | |
| 6,270,964 B1 | 8/2001 | Michnick et al. | |
| 6,294,330 B1 | 9/2001 | Michnick et al. | |
| 6,300,078 B1 | 10/2001 | Friend et al. | |
| 6,303,291 B1 | 10/2001 | Friend et al. | |
| 6,312,956 B1 | 11/2001 | Lane | |
| 6,322,973 B1 | 11/2001 | Bostian et al. | |
| 6,342,345 B1 | 1/2002 | Blau et al. | |
| 6,370,478 B1 | 4/2002 | Stoughton et al. | |
| 6,416,959 B1 | 7/2002 | Giuliano et al. | |
| 6,428,951 B1 | 8/2002 | Michnick et al. | |
| 6,453,241 B1 | 9/2002 | Bassett, Jr. et al. | |
| 6,482,603 B1 | 11/2002 | Dohlman et al. | |
| 6,518,021 B1 | 2/2003 | Thastrup et al. | |
| 6,548,263 B1 | 4/2003 | Kapur et al. | |
| 6,573,039 B1 | 6/2003 | Dunlay et al. | |
| 6,620,591 B1 | 9/2003 | Dunlay et al. | |
| 6,623,966 B1 | 9/2003 | Lane | |
| 6,633,662 B2 | 10/2003 | Ravkin | |
| 6,649,414 B1 | 11/2003 | Chandler et al. | |
| 6,656,695 B2 | 12/2003 | Berg et al. | |
| 6,671,624 B1 | 12/2003 | Dunlay et al. | |
| 6,716,588 B2 | 4/2004 | Sammak et al. | |
| 6,727,071 B1 | 4/2004 | Dunlay et al. | |
| 6,753,413 B1 | 6/2004 | Ching et al. | |
| 6,756,207 B1 | 6/2004 | Giuliano et al. | |
| 6,759,206 B1 | 7/2004 | Rubin et al. | |
| 6,763,307 B2 | 7/2004 | Berg et al. | |
| 6,780,599 B2 | 8/2004 | Hamilton et al. | |
| 6,801,859 B1 | 10/2004 | Friend et al. | |
| 6,839,635 B2 | 1/2005 | Bassett, Jr. et al. | |
| 6,859,735 B1 | 2/2005 | Stoughton et al. | |
| 6,875,578 B2 | 4/2005 | Giuliano et al. | |

(Continued)

FOREIGN PATENT DOCUMENTS

| | | |
|---|---|---|
| DE | 101 43 757 A1 | 3/2003 |
| EP | 1 184 463 A1 | 3/2002 |

(Continued)

OTHER PUBLICATIONS

Boyd, S.D., et al., "An Intact HDM2 RING-Finger Domain is Required for Nuclear Exclusion of p53," *Nature Cell Biology* 2:563-568 (Sep. 2000).

(Continued)

*Primary Examiner* — Lisa Cook
(74) *Attorney, Agent, or Firm* — Hamilton, Brook, Smith & Reynolds, P.C.

(57) ABSTRACT

The invention provides an improved method for identifying and interpreting tissue specimens and/or cells derived from tissue specimens. A panel of cell-based reagents provides a number of readouts of cellular states or biomarkers that together define a profile of a diversity of cellular states or biomarkers in a tissue specimen representing the 'systems" nature of biology. This cellular profile is interpreted using informatics tools, to identify similarities between specimens, in vivo medical conditions, and suggest options for treating medical conditions.

17 Claims, 11 Drawing Sheets

(56) References Cited

U.S. PATENT DOCUMENTS

| | | |
|---|---|---|
| 6,897,017 B1 | 5/2005 | Michnick et al. |
| 6,902,883 B2 | 6/2005 | Dunlay et al. |
| 6,929,916 B2 | 8/2005 | Michnick et al. |
| 6,939,720 B2 | 9/2005 | Chandler et al. |
| 6,950,752 B1 | 9/2005 | Friend et al. |
| 6,956,961 B2 | 10/2005 | Cong et al. |
| 6,973,388 B2 | 12/2005 | Friend et al. |
| 6,986,993 B1 | 1/2006 | Ghosh et al. |
| 7,054,755 B2 | 5/2006 | O'Reilly et al. |
| 7,060,445 B1 | 6/2006 | Dunlay et al. |
| 7,062,219 B2 | 6/2006 | Michnick et al. |
| 7,085,765 B2 | 8/2006 | Zock et al. |
| 7,117,098 B1 | 10/2006 | Dunlay et al. |
| 7,130,746 B2 | 10/2006 | Friend et al. |
| 7,160,687 B1 | 1/2007 | Kapur et al. |
| 7,166,424 B2 | 1/2007 | Michnick et al. |
| 7,176,287 B2 | 2/2007 | Hamilton et al. |
| 7,219,016 B2 | 5/2007 | Rimm et al. |
| 7,235,353 B2 | 6/2007 | Mattheakis et al. |
| 7,235,373 B2 | 6/2007 | Dunlay et al. |
| 7,244,614 B2 | 7/2007 | Bright et al. |
| 7,254,487 B2 | 8/2007 | Marton et al. |
| 7,266,458 B2 | 9/2007 | Plavec et al. |
| 7,269,278 B2 | 9/2007 | Cong et al. |
| 7,269,517 B2 | 9/2007 | Bondarenko |
| 7,274,809 B2 | 9/2007 | MacAulay et al. |
| 7,282,347 B2 | 10/2007 | Bjorn et al. |
| 7,294,466 B2 | 11/2007 | McMillan |
| 7,306,914 B2 | 12/2007 | Michnick et al. |
| 7,314,915 B2 | 1/2008 | Thastrup et al. |
| 8,114,615 B2 * | 2/2012 | Gough et al. ............... 435/7.21 |
| 2003/0040012 A1 | 2/2003 | Kato et al. |
| 2003/0044847 A1 | 3/2003 | Pestka et al. |
| 2003/0059093 A1 | 3/2003 | Rosania et al. |
| 2003/0096243 A1 | 5/2003 | Busa |
| 2004/0043436 A1 | 3/2004 | Vlahou et al. |
| 2004/0063162 A1 | 4/2004 | Dunlay et al. |
| 2004/0072269 A1 | 4/2004 | Rao et al. |
| 2004/0101912 A1 | 5/2004 | Rubin et al. |
| 2004/0146944 A1 | 7/2004 | Fang et al. |
| 2005/0014216 A1 | 1/2005 | Mattheakis et al. |
| 2005/0038608 A1 | 2/2005 | Chandra et al. |
| 2005/0059153 A1 | 3/2005 | George et al. |
| 2005/0136509 A1 | 6/2005 | Gholap et al. |
| 2005/0136549 A1 | 6/2005 | Gholap et al. |
| 2005/0154535 A1 | 7/2005 | Sun et al. |
| 2005/0165594 A1 | 7/2005 | Chandra et al. |
| 2005/0214826 A1 | 9/2005 | Mor et al. |
| 2005/0266395 A1 | 12/2005 | Gholap et al. |
| 2006/0014137 A1 | 1/2006 | Ghosh et al. |
| 2006/0014238 A1 | 1/2006 | Gholap et al. |
| 2006/0094868 A1 | 5/2006 | Giuliano et al. |
| 2006/0141539 A1 | 6/2006 | Taylor |
| 2006/0188140 A1 | 8/2006 | Gholap et al. |
| 2006/0265137 A1 | 11/2006 | Zock et al. |
| 2007/0019854 A1 | 1/2007 | Gholap et al. |
| 2007/0038385 A1 | 2/2007 | Nikolskaya et al. |
| 2007/0048746 A1 | 3/2007 | Su et al. |
| 2007/0072246 A1 | 3/2007 | Berg et al. |
| 2007/0083333 A1 | 4/2007 | Vitiello et al. |
| 2007/0087344 A1 | 4/2007 | Plavec et al. |
| 2007/0099219 A1 | 5/2007 | Teverovskiy et al. |
| 2007/0166771 A1 | 7/2007 | Kapur et al. |
| 2007/0172844 A1 | 7/2007 | Lancaster et al. |
| 2007/0178605 A1 | 8/2007 | Mor et al. |
| 2007/0212721 A1 | 9/2007 | Fischer et al. |
| 2008/0015786 A1 | 1/2008 | Ramer et al. |
| 2008/0020417 A1 | 1/2008 | Rosler et al. |
| 2008/0026415 A1 | 1/2008 | Rimm et al. |
| 2008/0026420 A1 | 1/2008 | Rimm et al. |
| 2008/0040044 A1 | 2/2008 | Dunlay et al. |
| 2008/0046190 A1 | 2/2008 | Rimm et al. |
| 2008/0057514 A1 | 3/2008 | Goldenring |
| 2009/0131270 A1 | 5/2009 | Taylor et al. |
| 2009/0170091 A1 | 7/2009 | Giuliano et al. |
| 2010/0009352 A1 | 1/2010 | Gough et al. |
| 2010/0112602 A1 | 5/2010 | Taylor et al. |

FOREIGN PATENT DOCUMENTS

| | | |
|---|---|---|
| JP | 2005-323573 | 11/2005 |
| WO | WO 97/14028 A2 | 4/1997 |
| WO | WO 97/14028 A3 | 4/1997 |
| WO | WO 97/45730 A1 | 12/1997 |
| WO | WO 98/38490 A1 | 9/1998 |
| WO | WO 98/44350 A1 | 10/1998 |
| WO | WO 99/28856 A1 | 6/1999 |
| WO | WO 99/36564 A1 | 7/1999 |
| WO | WO 99/44063 A2 | 9/1999 |
| WO | WO 99/55356 A1 | 11/1999 |
| WO | WO 99/58708 A1 | 11/1999 |
| WO | WO 99/59037 A1 | 11/1999 |
| WO | WO 99/66024 A1 | 12/1999 |
| WO | WO 00/03246 A2 | 1/2000 |
| WO | WO 00/03246 A3 | 1/2000 |
| WO | WO 00/17402 A1 | 3/2000 |
| WO | WO 00/17624 A2 | 3/2000 |
| WO | WO 00/17643 A2 | 3/2000 |
| WO | WO 00/17643 A3 | 3/2000 |
| WO | WO 00/20859 A1 | 4/2000 |
| WO | WO 00/26408 A2 | 5/2000 |
| WO | WO 00/39336 A1 | 7/2000 |
| WO | WO 00/39337 A1 | 7/2000 |
| WO | WO 00/39338 A1 | 7/2000 |
| WO | WO 00/39340 A1 | 7/2000 |
| WO | WO 00/50872 A2 | 8/2000 |
| WO | WO 00/60356 A1 | 10/2000 |
| WO | WO 00/70342 A2 | 11/2000 |
| WO | WO 00/70528 A2 | 11/2000 |
| WO | WO 00/70528 A3 | 11/2000 |
| WO | WO 00/79241 A2 | 12/2000 |
| WO | WO 01/07889 A2 | 2/2001 |
| WO | WO 01/07891 A2 | 2/2001 |
| WO | WO 01/11340 A1 | 2/2001 |
| WO | WO 01/11341 A2 | 2/2001 |
| WO | WO 01/20533 A2 | 3/2001 |
| WO | WO 01/20533 A3 | 3/2001 |
| WO | WO 01/33228 A2 | 5/2001 |
| WO | WO 01/33228 A3 | 5/2001 |
| WO | WO 01/35072 A2 | 5/2001 |
| WO | WO 01/42786 A2 | 6/2001 |
| WO | WO 01/81895 A2 | 11/2001 |
| WO | WO 01/81895 A3 | 11/2001 |
| WO | WO 02/18537 A2 | 3/2002 |
| WO | WO 02/27031 A2 | 4/2002 |
| WO | WO 02/31704 A1 | 4/2002 |
| WO | WO 02/50512 A2 | 6/2002 |
| WO | WO 02/50512 A3 | 6/2002 |
| WO | WO 02/052272 A2 | 7/2002 |
| WO | WO 02/052272 A3 | 7/2002 |
| WO | WO 02/057297 A1 | 7/2002 |
| WO | WO 02/067182 A2 | 8/2002 |
| WO | WO 02/067182 A3 | 8/2002 |
| WO | WO 02/067195 A2 | 8/2002 |
| WO | WO 02/067195 A3 | 8/2002 |
| WO | WO 02/073200 A1 | 9/2002 |
| WO | WO 02/077903 A2 | 10/2002 |
| WO | WO 02/086450 A2 | 10/2002 |
| WO | WO 02/086450 A3 | 10/2002 |
| WO | WO 03/012068 A2 | 2/2003 |
| WO | WO 03/012068 A3 | 2/2003 |
| WO | WO 03/023573 A2 | 3/2003 |
| WO | WO 03/023573 A3 | 3/2003 |
| WO | WO 03/029827 A2 | 4/2003 |
| WO | WO 03/029877 A1 | 4/2003 |
| WO | WO 03/066876 A2 | 8/2003 |
| WO | WO 03/066876 A3 | 8/2003 |
| WO | WO 03/079024 A1 | 9/2003 |
| WO | WO 2004/031765 A1 | 4/2004 |
| WO | WO 2004/076643 A2 | 9/2004 |
| WO | WO 2004/076643 A3 | 9/2004 |
| WO | WO 2004/092336 A2 | 10/2004 |
| WO | WO 2004/092336 A3 | 10/2004 |

(56) References Cited

FOREIGN PATENT DOCUMENTS

| | | |
|---|---|---|
| WO | WO 2004/094609 A2 | 11/2004 |
| WO | WO 2004/094609 A3 | 11/2004 |
| WO | WO 2004/094992 A2 | 11/2004 |
| WO | WO 2004/094992 A3 | 11/2004 |
| WO | WO 2005/008242 A1 | 1/2005 |
| WO | WO 2005/023987 A2 | 3/2005 |
| WO | WO 2005/023987 A3 | 3/2005 |
| WO | WO 2005/050556 A2 | 6/2005 |
| WO | WO 2005/050563 A2 | 6/2005 |
| WO | WO 2005/050563 A3 | 6/2005 |
| WO | WO 2005/055113 A2 | 6/2005 |
| WO | WO 2005/055113 A3 | 6/2005 |
| WO | WO 2005/075669 A1 | 8/2005 |
| WO | WO 2005/083440 A2 | 9/2005 |
| WO | WO 2005/083440 A3 | 9/2005 |
| WO | WO 2005/091203 A2 | 9/2005 |
| WO | WO 2005/091203 A3 | 9/2005 |
| WO | WO 2005/093561 A1 | 10/2005 |
| WO | WO 2005/095964 A2 | 10/2005 |
| WO | WO 2005/095964 A3 | 10/2005 |
| WO | WO 2005/100588 A2 | 10/2005 |
| WO | WO 2005/100588 A3 | 10/2005 |
| WO | WO 2005/106764 A2 | 11/2005 |
| WO | WO 2005/106764 A3 | 11/2005 |
| WO | WO 2006/010047 A2 | 1/2006 |
| WO | WO 2006/010047 A3 | 1/2006 |
| WO | WO 2006/017751 A2 | 2/2006 |
| WO | WO 2006/017751 A3 | 2/2006 |
| WO | WO 2006/020627 A1 | 2/2006 |
| WO | WO 2006/023576 A2 | 3/2006 |
| WO | WO 2006/023576 A3 | 3/2006 |
| WO | WO 2006/036726 A1 | 4/2006 |
| WO | WO 2006/036737 A2 | 4/2006 |
| WO | WO 2006/036737 A3 | 4/2006 |
| WO | WO 2006/037622 B1 | 4/2006 |
| WO | WO 2006/058014 A2 | 6/2006 |
| WO | WO 2006/058014 A3 | 6/2006 |
| WO | WO 2006/084272 A2 | 8/2006 |
| WO | WO 2006/105147 A2 | 10/2006 |
| WO | WO 2006/113529 A2 | 10/2006 |
| WO | WO 2006/113529 A3 | 10/2006 |
| WO | WO 2007/044944 A1 | 4/2007 |
| WO | WO 2007/047450 A1 | 4/2007 |
| WO | WO 2007/080583 A2 | 7/2007 |
| WO | WO 2007/081968 A1 | 7/2007 |
| WO | WO 2007/084374 A2 | 7/2007 |
| WO | WO 2007/090076 A2 | 8/2007 |
| WO | WO 2007/090076 A3 | 8/2007 |
| WO | WO 2007/092547 A2 | 8/2007 |
| WO | WO 2007/103374 A2 | 9/2007 |
| WO | WO 2007/103406 A2 | 9/2007 |
| WO | WO 2007/103406 A3 | 9/2007 |
| WO | WO 2007/103492 A2 | 9/2007 |
| WO | WO 2007/103531 A2 | 9/2007 |
| WO | WO 2007/103532 A2 | 9/2007 |
| WO | WO 2007/103535 A2 | 9/2007 |
| WO | WO 2007/126631 A1 | 11/2007 |
| WO | WO 2007/130677 A2 | 11/2007 |
| WO | WO 2007/136724 A2 | 11/2007 |
| WO | WO 2007/136724 A3 | 11/2007 |
| WO | WO 2007/139895 A2 | 12/2007 |
| WO | WO 2008/008500 A2 | 1/2008 |
| WO | WO 2008/018905 A2 | 2/2008 |
| WO | WO 2008/018905 A3 | 2/2008 |
| WO | WO 2008/042487 A1 | 4/2008 |
| WO | WO 2008/060483 A2 | 5/2008 |
| WO | WO 2008/115420 A2 | 9/2008 |
| WO | WO 2009/002565 A1 | 12/2008 |

OTHER PUBLICATIONS

Byrne, L., et al., "The Use of Fluorescent in Situ Hybridisation (FISH) on Paraffin Embedded Tissue Section (PETS) in a Routine Diagnostic Laboratory. The Use of Fluorescent in Siti Hybridisation (FISH) on Paraffin Embedded Tissue Sections (PETS) in a Routine Diagnostic Labo," *Journal of Medical Genetics*, vol. 39, Supp. 1., p. S53, XP009093426; and British Human Genetics Conference, York, England, Sep. 23-25, 2002, ISSN: 0022-2593.

Callaway, et al., "Quantifying ERK2-Protein Interactions by Fluorescence Anisotropy: PEA-15 Inhibits ERK2 by Blocking the Binding of DEJL Domains," *Biochimica et Biophysica Acta (BBA)—Proteins & Protemoics*, 1754(1-2):316-323 (Dec. 2005), XP005214221, ISSN: 15709639.

Giuliano, K.A., et al., "Fluorescent Protein Biosensors," *Modern Drug Discovery*, pp. 33-37 (Aug. 2003).

Giuliano, K.A., et al., "Optimal Characteristics of Protein-Protein Interaction Biosensors for Cellular Systems Biology Profiling," Preprint to be published in High Content Screening: Science, Technology and Applications, ed. Haney, S.A., Wiley Publishers, (2007), Retrieved from the Internet: url:http://www.cellumen.com/downloads/cellumen-2007-Giuliano-PPIBs.pdf; [retrieved on Sep. 1, 2008].

Giuliano, K.A., et al., "Reagents to Measure and Manipulate Cell Functions," *Methods in Molecular Biology*, 356:141-163 (Jan. 2007), XP009097250, ISSN: 1064-3745.

Giuliano, K.A., et al., "Systems Cell Biology Based on High-Content Screening," *Methods in Enzymology*, Elsevier Academic Press, Inc., pp. 601-619 (2006), XP009097131, ISSN: 0-12-182819-0(H).

Giuliano, K.A., et al., "Systems Cell Biology Knowledge Created from High Content Screening," *Assay and Drug Development Technologies*, 3(5):501-514 (Oct. 2005) XP002473054, ISSN: 1540-658X.

Henderson, B.R. and Eleftheriou, A., "A Comparison of the Activity, Sequence Specificity, and CRM1-Dependence of Different Nuclear Export Signals," *Experimental Cell Research* 256:213-224 (2000).

Hodel, M.R., et al., "Dissection of a Nuclear Localization Signal," *Journal of Biological Chemistry* 276(2):1317-1325 (Jan. 2001).

Kennedy, S.W., et al., "Cytochrome P4501A Inductino in Avian Hepatocyte Cultures: A Promising Approach for Predicting the Sensitivity of Avian Species to Toxic Effects of Halogenated Aromatic Hydrocarbons," *Toxicology and Applied Pharmacology*, 141(1):214-230 (Apr. 1996).

Lin, H., et al., "Involvement of Cdk5/p25 in Digoxin-Triggered Prostate Cancer Cell Apoptosis," *Journal of Biological Chemistry*, 279(28):29302-29307 (2004), XP002483342.

Liu, J., et al., "Src Homology 3 Binding Sites in the P262 Nucleotide Receptor Interact with Src and Regulate Activities of Src, Proline-rich Tyrosine Kinase 2, and Growth Factor Receptors," *Journal of Biological Chemistry*, 279(9):8212-8218 (2004) XP002483344.

Lopez-Sanchez, Carmen, et al., "Rapid Triple-Labelling Method Combining in Situ Hybridization and Double Immunocytochemistry," *Developmental Dynamics*, 230(2):309-315 (Jun. 2004), XP009093410 ISSN: 1058-8388.

Martinez, J-C, et al., "HDM2 Overexpression and Focal Loss of p14/ARF expression may Deregulate the p53 Tumour Suppressor Pathway in Meningeal Haemangiopericytomas. Study by Double Immunofluorescence and Laser Scanning Confocal Microscopy," *Histopathology*, 46(2):184-194 (2005) XP002483343.

O'Brien, P.J., et al., "High Concordance of Drug-Induced Human Hepatotoxicity with in vitro Cytotoxicity Measured in a Novel Cell-based Model Using High Content Screening," *Arch. Toxicol*, 80(9):580-604 (Apr. 2006).

Poynard, Thierry, et al., "The Diagnostic Value of Biomarkers (SteatoTest) for the Prediction of Liver Steatosis," *Comparative Hepatology*, 4:1-14 (Dec. 2005).

Sudar, D., et al., "Microscopy Environment for Quantitative Spatial and Temporal Analysis of Multicellular Interactions," *Proceedings of the SPIE—The International Society for Optical Engineering SPIE—Int. Soc. Opt. Eng USA*, 4621:47-51 (2002), XP002466769, ISSN: 0277-786X.

Tanaka, M., et al., "An Unbiased Cell Morphology-Based Screen for New, Biologically Active Small Molecules," *PLOS Biology*, vol. 3, No. 5, p. e128 (May 2005); XP002473053 ISSN: 1545-7885, p. 0765.

Taylor, L.D., et al., "Potenial of Machine-Vision Light Microscopy in Toxicologic Pathology," *Toxicologic Pathology*, 22(2):145-159 (1994), XP009093339 ISSN: 0192-6233.

(56) References Cited

OTHER PUBLICATIONS

Uchihara, T., et al., "Triple Immunofluorolabeling with Two Rabbit Polyclonal Antibodies and a Mouse Monoclonal Antibody allowing three-dimensional analysis of Cotton Wool Plaques in Alzheimer Disease," *Journal of Histochemistry & Cytochemistry*, 51(9):1201-1206 (Sep. 2003), XP002461783 ISSN: 0022-1554.
Notification of Transmittal of the International Search Report and the Written Opinion of the International Searching Authority for . PCT/US2007/011865, "Method for Automated Tissue Analysis", date of mailing Jan. 11, 2008.
Notification of Transmittal of the International Preliminary Report on Patentability for PCT/US2007/011865, "Method for Automated Tissue Analysis", date of mailing Jan. 11, 2008.
Invitation to Pay Additional Fees with Partial International Search Report for PCT/US2007/012406, "Method for Modeling a Disease", date of mailing Feb. 13, 2008.
Notification of Transmittal of the International Search Report and the Written Opinion of the International Searching Authority for PCT/US2007/012406, "Method for Modeling a Disease", date of mailing Apr. 8, 2008.
Notification of Transmittal of the International Preliminary Report on Patentability for PCT/US2007/012406, "Method for Modeling a Disease", date of mailing Nov. 28, 2008.
Invitation to Pay Additional Fees with Partial International Search Report for PCT/US2007/023678, "Protein-Protein Interaction Biosensors and Methods of Use Thereof", date of mailing Jun. 19, 2008.
Notification of Transmittal of the International Search Report and the Written Opinion of the International Searching Authority for PCT/US2007/023678, "Protein-Protein Interaction Biosensors and Methods of Use Thereof", date of mailing Aug. 29, 2008.
Notification of Transmittal of the International Preliminary Report on Patentability for PCT/US2007/001217, "Method for Predicting Biological Systems Responses", date of mailing Aug. 12, 2008.
Notification of Transmittal of the International Search Report and the Written Opinion of the International Searching Authority for PCT/US2007/001217, "Method for Predicting Biological Systems Responses", date of mailing Mar. 31, 2008.
Amendment Under Article 34 and Reply to Written Opinion for PCT/US2007/001217, "Method for Predicting Biological Systems Responses", date of mailing Jun. 30, 2008.
Notification of Transmittal of the International Search Report and the Written Opinion of the International Searching Authority for PCT/US2005/27919, "Methods for the Detection of Molecular Interactions", date of mailing Oct. 17, 2006.
Notification of Transmittal of the International Preliminary Report on Patentability for for PCT/US2005/27919, "Methods for the Detection of Molecular Interactions", date of mailing Feb. 15, 2007.
Communication with Supplementary Partial European Search Report for EP 05 77 8448, "Methods for the Detection of Molecular Interactions", date of mailing Sep. 15, 2008.
Notification of Transmittal of the International Search Report and the Written Opinion of the International Searching Authority for PCT/US2008/008105, "Method for Predicting Biological Systems Responses in Hepatocytes", date of mailing Oct. 24, 2008.
Notification of Transmittal of the International Search Report and the Written Opinion of the International Searching Authority for PCT/US2008/00340, "Methods for Detecting Molecular Interactions Within Cells Using Combination of Inducible Promoters and Biosensors", date of mailing Sep. 4, 2008.
Notification Concerning Transmittal of the International Preliminary Report on Patentability for PCT/US2007/023678, "Protein-Protein Interaction Biosensors and Methods of Use Thereof", date of mailing May 22, 2009.
Office Action for EP 05 778 448.0, "Methods for the Detection of Molecular Interactions", date of mailing Sep. 3, 2009.
Office Action, EP 05 778 448.0, "Methods for the Detection of Molecular Interactions", date of mailing Dec. 19, 2008.
Reply to Office Action, EP 05 778 448.0, "Methods for the Detection of Molecular Interactions", date of mailing Jun. 29, 2009.
Notification of Transmittal of the International Preliminary Report on Patentability for PCT/US2008/008105, "Method for Predicting Biological Systems Responses in Hepatocytes", date of mailing Jan. 14, 2010.
Office Action, (Restriction Requirement)for U.S. Appl. No. 11/573,121, "Methods for the Detection of Molecular Interactions", date of mailing Nov. 20, 2009.
Reply to Office Action (Restriction Requirement) for U.S. Appl. No. 11/573,121, "Methods for the Detection of Molecular Interactions", filed Dec. 14, 2009.
Office Action, (Restriction Requirement), for U.S. Appl. No. 11/573,121, "Methods for the Detection of Molecular Interactions",date of mailing Jan. 22, 2010.
Reply to Office Action, (Restriction Requirement), for U.S. Appl. No. 11/573,121, "Methods for the Detection of Molecular Interactions",date of mailing Jul. 22, 2010.
Office Action for U.S. Appl. No. 11/573,121, "Methods for the Detection of Molecular Interactions",date of mailing Sep. 22, 2010.
Notice of Abandonment, for U.S. Appl. No. 11/573,121, "Methods for the Detection of Molecular Interactions",date of mailing May 24, 2011.
Office Action for EP 08 779 870.8, "Method for Predicting Biological Systems Responses in Hepatocytes", date of mailing Jun. 22, 2010.
Communication pursuant to Article 94(3) for EPC, 07795296.8, "Method for Modeling a Disease", date of mailing Jun. 15, 2010.
Loss of Rights for EP 07777137.6, "Method for Automated Tissue Analysis", date of mailing Jan. 13, 2010.
Reply to Loss of Rights for EP 07777137.6, "Method for Automated Tissue Analysis", date of mailing Mar. 12, 2010.
Examiner's invitation for EP 07777137.6, "Method for Automated Tissue Analysis", date of mailing Apr. 7, 2010.
Reply for EP 07777137.6"Method for Automated Tissue Analysis", filed Jun. 17, 2010.
Communication pursuant to Article 94(3) EPC for EP 07777137.6, "Method for Automated Tissue Analysis", date of mailing Sep. 13, 2010.
Reply to Office Action for EP 07 777 137.6, "Method for Automated Tissue Analysis", filed Mar. 23, 2011.
Summons to attend oral proceedings pursuant to Rule 115(1) EPCfor EP 07 777 137 6, "Method for Automated Tissue Analysis", date of mailing Apr. 29, 2011.
Communication pursuant to Article 94(3) EPC for EP 07867408.2, "Protein-Protein Interaction Biosensors and Methods of Use Thereof", date of mailing Feb. 23, 2010.
Reply to EPC for EP 07967408.2, "Protein-Protein Interaction Biosensors and Methods of Use Thereof", Filed Dec. 30, 2010.
Examination Report for EP 07835667.2, "Method for Predicting Biological Systems Responses", date of mailing Jun. 15, 2009.
Reply for EP 07835667.2, "Method for Predicting Biological Systems Responses", filed Dec. 22, 2009.
Supplemental Reply for EP 07835667.2, "Method for Predicting Biological Systems Responses", filed Jan. 6, 2010.
Office Action for EP 07 777 137.6, "Method for Automated Tissue Analysis", date of mailing May 26, 2009.

\* cited by examiner

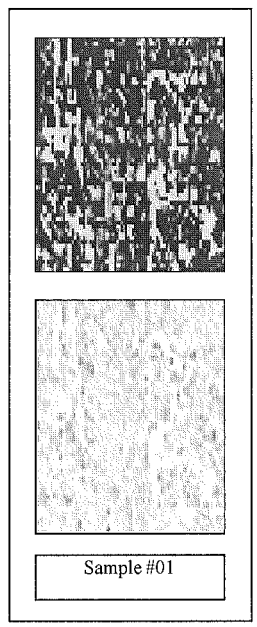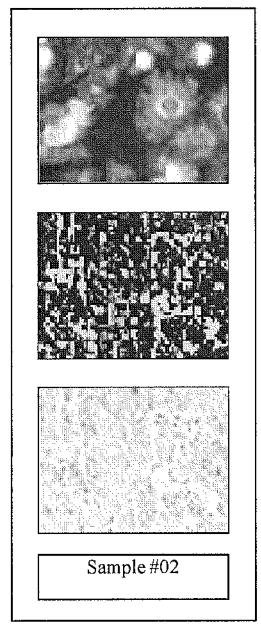

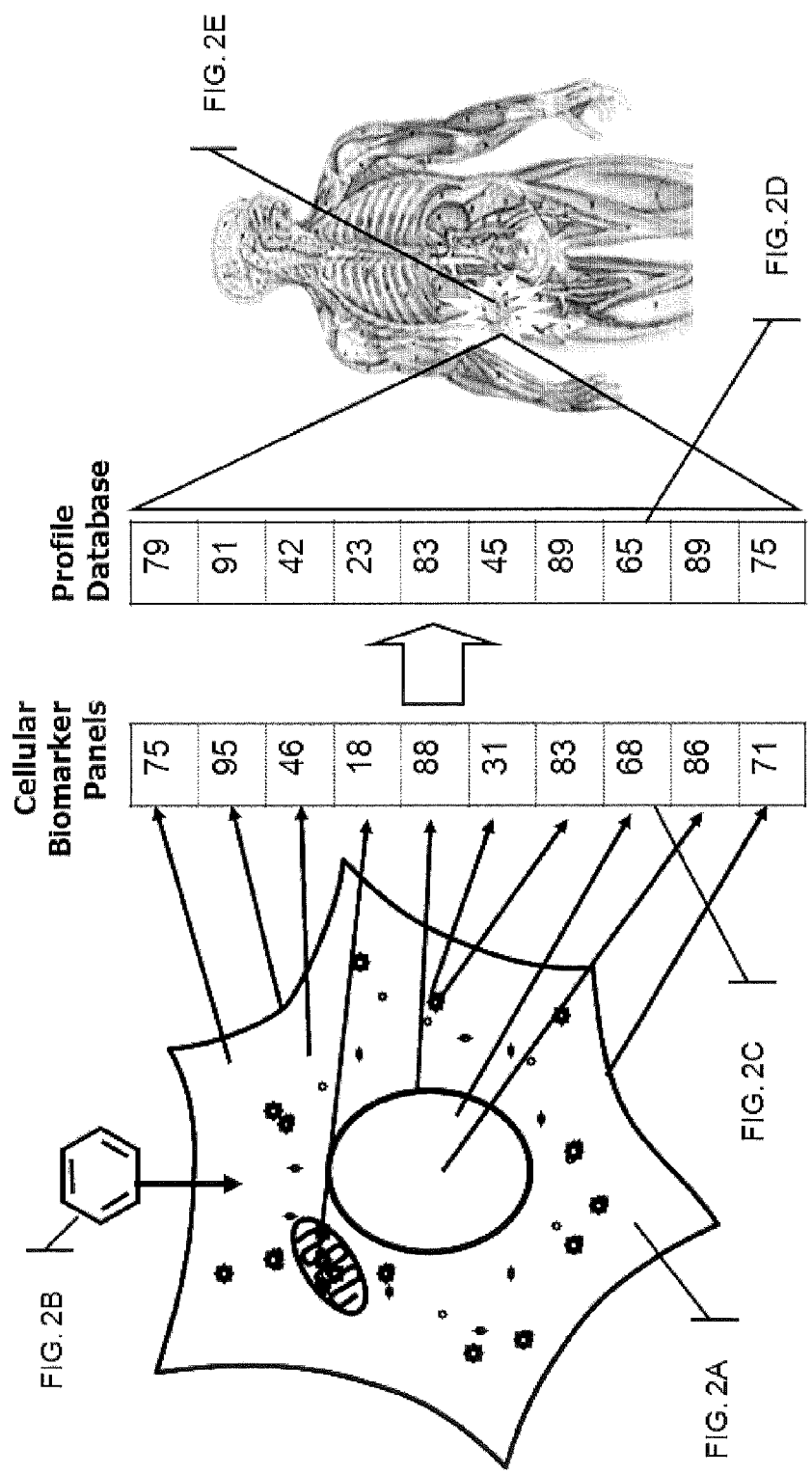

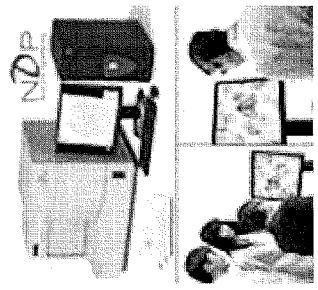
FIG. 11A
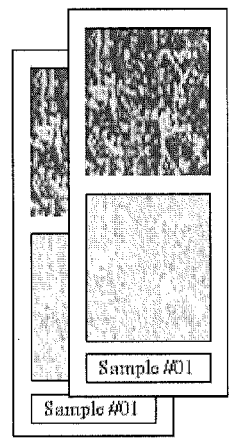
FIG. 11B
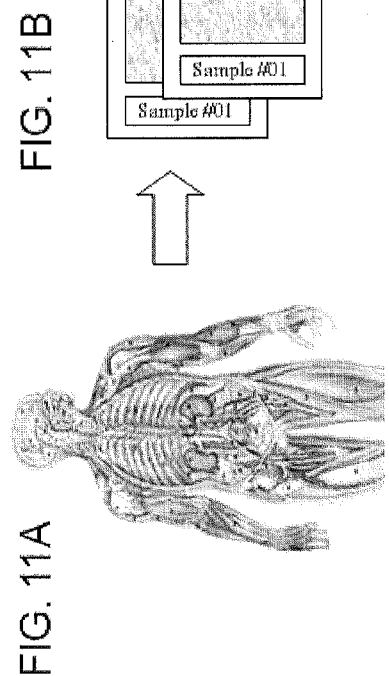
FIG. 11C
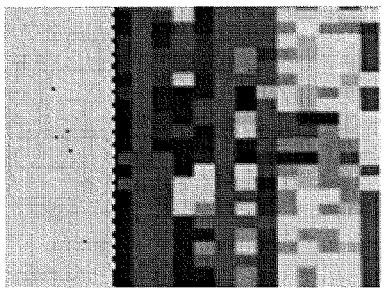
FIG. 11D
FIG. 11E
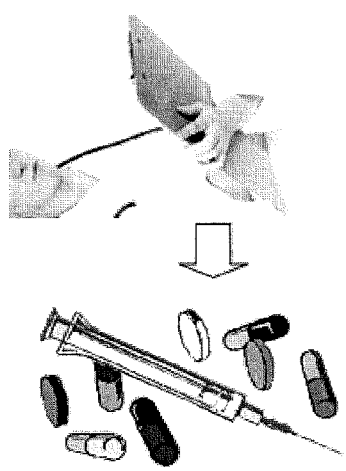
FIG. 11F
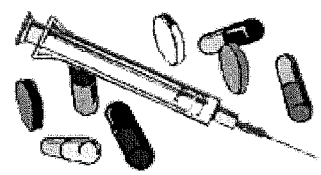
FIG. 11G
FIG. 11

METHOD FOR AUTOMATED TISSUE ANALYSIS

RELATED APPLICATION

This application is a continuation of U.S. application Ser. No. 13/346,920 filed Jan. 10, 2012 now abandoned, which is a continuation of U.S. application Ser. No. 12/227,334 filed Apr. 14, 2009 now U.S. Pat. No. 8,114,615, which is the U.S. National Stage of International Application No. PCT/US2007/011865 filed May 17, 2007, published in English, which claims the benefit of U.S. Provisional Application No. 60/801,035, filed on May 17, 2006.

The entire teachings of the above applications are incorporated herein by reference.

BACKGROUND OF THE INVENTION

The development of capabilities in multicolor fluorescence for applications in pathology were introduced more than a decade ago [3, 6-8] but still have not achieved wide market acceptance. In particular, Dow et al. [7] describe a study where multicolor fluorescence was used to determine lymphocyte phenotype and activation status in melanoma tissue sections through a process of human interactive image analysis. More recently, multicolor fluorescence has been applied in pathology [9] and HistoRx, Inc. (New Haven, Conn.) has commercialized some of these approaches. All of these publications and applications describe the use of fluorescence based imaging technology in tissue cell analysis, but are limited in their application and do not address the need to understand the systemic or cellular systems biology of a tissue.

High content screening (HCS) and multiparameter HCS technologies were developed to automate cell analysis for drug discovery, HCS technologies are focused specifically on the measurement of individual targets or pathways in arrays of cultured cells treated with test compounds. However, HCS tools alone do not address the complete workflow of tissue based cellular systems biology.

Thus, a need exists to provide methods for producing and analyzing cellular systems biology profiles in order to more fully understand the systemic and complex interaction of cellular biology systems.

SUMMARY OF THE INVENTION

The cell is the simplest living system. Tissues are collections of specific cell types forming interacting colonies of cells. Although cells and tissues are less complex than a complete organism, they possess significant functional complexity allowing a detailed understanding of many aspects affecting a whole organism, such as the cellular basis of disease, treatment efficacy and potential toxicity of treatments. Multicolor fluorescence of multiplexed biomarkers coupled with searchable databases provides the basis for cellular systems biology (also referred to herein as systems cell biology) profiling and analysis.

This invention provides for methods of analyzing and profiling, the analysis of, and means for profiling, tissue-based cellular systems biology. The cellular systems biology approach, including the combining of traditional histological staining with fluorescent staining to associate cellular and tissue markers that can be labeled by fluorescence has not been previously applied by others as now described herein. The use of the transmitted light images based on traditional histological stains used by pathologist as a "reference" image or "map" for better interpretation of the multiple fluorescence-based reagents as described herein will increase the acceptance of the systems approach by pathologists and will allow selection of a particular set of biomarkers for fluorescence analysis.

In one embodiment of the invention, provided is a method for producing a cellular systems biology profile of one or more tissue samples. As used herein, "cellular systems biology" (also referred to herein as systems cell biology), is the investigation of the integrated and interacting networks of genes, proteins, and metabolites that are responsible for normal and abnormal cell functions. Thus, a cellular systems biology profile is a systemic characterization of cells in the context of a tissue architecture such that the cells have particular characteristics dependent upon the relationships of different cells within a tissue and the biological or medical state of the tissue. It is the interactions, relationships, and state of the constituents of cells within a tissue that gives rise to the cellular systems biology features that are used to construct a profile. The interrelationships within a cellular systems biology profile are defined, for example, either arithmetically (e.g., ratios, sums, or differences between cellular systems biology feature values) or statistically (e.g., hierarchical clustering methods or principal component analyses of combinations of cellular systems biology feature values). In a particular embodiment, a cellular systems biology profile defines the interrelationships between a combination of at least five cellular systems biology features collected from cells within one or more tissue sections from the same sample.

In one embodiment, the invention is directed to a method for producing one or more cellular systems biology profiles for one or more tissue samples, comprising obtaining at least two sections from one or more tissue samples. At least one section is labeled with a histological stain, to produce a histologically stained section. At least one other section is labeled with a panel of fluorescently labeled reagents to produce a fluorescently labeled section. In some embodiments the histologically stained section and the fluorescently stained section are the same or different. In a particular embodiment, the histologically stained section and the fluorescently stained section are different section. Each fluorescently labeled reagent is specific for a biomarker. As used herein, a "biomarker" is a molecule which provides a measure of cellular and/or tissue function. For example, and without limitation, a biomarker can be the measure of estrogen receptor expression levels, Her2/neu expression, transcription factor activation, location or amount or activity of a protein, polynucleotide, organelle, and the like, the phosphorylation status of a protein, etc. In one embodiment of the invention, the panel of fluorescently labeled reagents detects at least about four different biomarkers.

The detection of a biomarker in one or more sections is a read-out of one or more features of the tissue. As used herein, a "feature" is a characteristic which provides a measurement or series of measurements of a particular biomarker (which can indicate a biological function) made in time and/or space within cells and tissues. Biological functions include, but are not limited to: protein posttranslational modifications such as phosphorylation, proteolytic cleavage, methylation, myristoylation, and attachment of carbohydrates; translocations of ions, metabolites, and macromolecules between compartments within or between cells; changes in the structure and activity of organelles; and alterations in the expression levels of macromolecules such as coding and non-coding RNAs and proteins, morphology, state of differentiation, and the like. A single biomarker can provide a read-out of more than one feature. For example, Hoechst dye can be used to detect DNA (e.g., a biomarker), and a number of features of the tissue (e.g., nucleus size, cell cycle stage, number of nuclei, presence of apoptotic nuclei, etc.) can be identified by the DNA detected with the Hoechst dye.

The method further comprises imaging the histologically stained section using a first optical mode, which produces a first set of data and imaging the fluorescently labeled section using a second optical mode, which produces a second set of data. The first set of data and the second set of data are analyzed to identify five or more features, such that at least one feature is identified in each of the first set of data and the second set of data. The combination of the five or more features generates a cellular systems biology profile of the one or more tissue samples.

In a further embodiment of the invention, the cellular systems biology profile is stored in a database for reference, thereby providing a reference cellular systems biology profile in a database.

In a further embodiment of the invention, the method for producing a cellular systems biology profile of one or more tissue samples further comprises producing a cellular systems biology profile of at least one peripheral blood sample obtained from the same source as the one or more tissue samples In another embodiment the method for producing a cellular systems biology profile of one or more tissue samples comprises obtaining at least one section from one or more tissue samples. At least one section is labeled with a panel of fluorescently labeled reagents to produce a fluorescently labeled section, such that each fluorescently labeled reagent is specific for a biomarker. In one embodiment, the panel of fluorescently labeled reagents detects at least about four different biomarkers, and the detection of a biomarker is a read-out of one or more features of a cellular systems biology profile. The method further comprises imaging the fluorescently labeled section with at least a first optical mode to produce a first set of data which is analyzed to identify at least about five or more features, wherein at least one feature is identified in the first set of data, and wherein the combination of the five or more features is a cellular systems biology profile the one or more tissue samples. Thus, the method produces a cellular systems biology profile of the one or more tissue samples. The method can further comprises producing a cellular systems biology profile of at least one peripheral blood sample obtained from the same source as the one or more tissue samples.

In a further embodiment of the invention, provided herein is a method for producing a cellular systems biology profile of one or more tissue samples, wherein the tissue sample is profiled for the presence of cancer, the stage of a cancer, the diagnosis of a cancer, the prognosis of a cancer and/or the absence of a cancer. As will be understood by a person of skill in the art, different cancers can be classified and staged according to their pathology. The method described herein permits, for example, the confirmation of the presence or absence of a cancer, the identification of a cancer, the classification of a cancer stage, the prediction and/or determination of the outcome or prognosis of the cancer, and the response of the cancer to any treatments. The method comprises obtaining at least two sections from one or more tissue samples. At least one section is labeled with a histological stain to produce a histologically stained section. At least one section is labeled with a panel of fluorescently labeled reagents to produce a fluorescently labeled section. Each fluorescently labeled reagent is specific for a biomarker. The panel of fluorescently labeled reagents comprises fluorescently labeled reagents which can be selected from the group consisting of: i) one or more fluorescently labeled reagents specific for at least four cancer cell biomarkers; ii) one or more fluorescently labeled reagents specific for at least four migratory immune cell biomarkers; iii) a combination of A) one or more fluorescently labeled reagents specific for at least three cancer cell biomarkers and B) one or more fluorescently labeled reagents specific for at least three migratory immune cell biomarkers, and iv) combinations of the above, such that the panel of fluorescently labeled reagents detects at least about four different biomarkers. The detection of a biomarker is a read-out of one or more features of a cellular systems biology profile. The method further comprises imaging the histologically stained section with at least a first optical mode to produce a first set of data and imaging the fluorescently labeled section with at least a second optical mode to produce a second set of data. The first set of data and second set of data are analyzed to identify at least about five or more features, such that at least one feature is identified in each of the first set of data and the second set of data. The combination of the five or more features is a cellular systems biology profile of the one or more tissue samples, and thus the method produces a cellular systems biology profile of the one or more tissue samples, wherein the tissue sample is profiled for the presence of a cancer, the stage of a cancer, the diagnosis of a cancer, the prognosis of a cancer or the absence of a cancer. In one embodiment, the one or more tissue samples is selected from the group consisting a suspected or known cancerous tissue, a lymph node, and a combination thereof.

In a still further embodiment of the invention, the method for producing a cellular systems biology profile of one or more tissue samples, wherein the tissue sample is profiled for the presence of cancer, the stage of a cancer, the diagnosis of a cancer, the prognosis of a cancer and/or the absence of a cancer further comprises producing a cellular systems biology profile of at least one peripheral blood sample obtained from the same source as the one or more tissue samples In another embodiment of the invention, provided herein is a method for producing a cellular systems biology profile of one or more tissue samples, wherein the tissue sample is profiled for the presence, severity or absence of a tissue toxicity. The method comprises obtaining at least two sections from one or more tissue samples. At least one section labeled with a histological stain to produce a histologically stained section and at least one section is with a panel of fluorescently labeled reagents to produce a fluorescently labeled section. Each fluorescently labeled reagent is specific for a biomarker. The panel of fluorescently labeled reagents comprises a set of fluorescently labeled reagents selected from the group consisting of i) one or more fluorescently labeled reagents specific for cell metabolism biomarkers, ii) one or more fluorescently labeled reagents specific for DNA damage biomarkers, iii) one or more fluorescently labeled reagents specific for cell morphology biomarkers, iv) one or more fluorescently labeled reagents specific for DNA damage biomarkers, v) one or more fluorescently labeled reagents specific for cell differentiation biomarkers, vi) one or more fluorescently labeled reagents specific for stress-induced transcription activation or inhibition biomarkers, vii) a one or more fluorescently labeled reagents specific for phosphorylation status of stress kinase biomarkers, viii) one or more fluorescently labeled reagents specific for apoptosis or necrosis biomarkers, ix) one or more fluorescently labeled reagents specific for cytoskeleton biomarkers, x) one or more fluorescently labeled reagents specific for organelle biomarkers, xi) one or more f fluorescently labeled reagents specific for presence or activation of immune cell biomarkers, and xii) combinations thereof, such that the panel of fluorescently labeled reagents detects at least about four different biomarkers, and wherein the detection of a biomarker is a read-out of one or more features of a cellular systems biology profile. The histologically stained section is imaged with at least a first optical mode to produce a first set of data. The fluorescently labeled section is imaged with at least a second optical mode to produce a second set of data. The method further comprises analyzing the first set of data and second set of data to identify at least about five or more features, wherein at least one feature is identified in each of the first set of data and the second set of data. The combination of the five or more features is a cellular systems biology profile of the one or more tissue samples. Thus, the method produces a cellular systems biology profile of the one or more tissue samples, wherein the tissue sample is profiled for the presence, severity or absence of a tissue toxicity. In one embodiment, the one or more tissue samples is one or more liver tissue samples.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 are examples of slides for Tissue Profiling. FIG. 1A is Sample #01, which represents a slide that combines a tissue section labeled with H&E stain, and a sequential section labeled with fluorescent tags for specific biomarkers. FIG. 1B is Sample #02, which illustrates a slide with an H&E stained section, a fluorescent labeled section and some cells isolated from patient tissue and labeled with fluorescent tags (pictures of sections and cells are all enlarged for illustrative purposes).

FIG. 2 is a schematic of systems cell biology (also referred to herein as cellular systems biology) profiling, which involves the analysis of a diverse set of cellular biomarkers used to identify features to create a profile. FIG. 2A represent cells from a patient that are, e.g., healthy, diseased or being treated or have been treated with a drug. FIG. 2B schematically represents the analysis of a set of biomarkers. FIG. 2C represents a panel of cellular biomarkers used to produce cellular systems biology profile. These profiles are stored in a database (schematically shown in FIG. 2D), which can be used a reference database. Comparison of a patient profile with reference profiles is used e.g., as a predictive tool, or to associate a biomarker, feature or a profile with a specific medical condition, or to evaluate new profiles (schematically represented in FIG. 2E).

FIG. 9(A) Process starts with reference tissue with know medical history. FIG. 9(B) Profiles from fluorescence analysis are combined with results from human interpretation of stained sections along with medical history; FIG. 9(C) to build a classifier and FIG. 9(D) populate a reference database. FIG. 9(E) Patient tissues are FIG. 9(F) prepared, analyzed and FIG. 9(G) classified to identify FIG. 9(H) similarities to other patient profiles (patient stratification) and FIG. 9(I) to make predictions regarding medical conditions, or medical outcomes.

FIG. 11 is an overview of one embodiment of the invention. Tissue samples from a patient (A) which could include healthy tissue, tumor tissue, other diseased tissue or a blood specimen are processed by standard methods for mounting on slides (B) either as individual sections or as tissue microarrays. Slides are imaged on a microscope or other imaging system (C). Images are interpreted either by a pathologist or through the application of image analysis algorithms to produce data (D) which can be stored in a database. The combination of the data from a single specimen forms a cellular systems profile of that specimen. Data from multiple cellular systems profiles are analyzed using statistical methods including cluster analysis, principle component analysis, and other multifactorial methods to identify similarities between profiles which can be represented in a clustered heat map (E), identify patterns within a profile that indicate a certain biological or medical state, and to classify tissue status based on similarity in profiles. The information provided by cellular systems biology profiling is used by the physician or scientist (F) to better understand the biology or progression of a disease or biological condition, to more precisely stratify patients in a clinical trial and/or to optimize a therapeutic approach (G) to treating a condition.

DETAILED DESCRIPTION OF THE INVENTION

Figure 3:
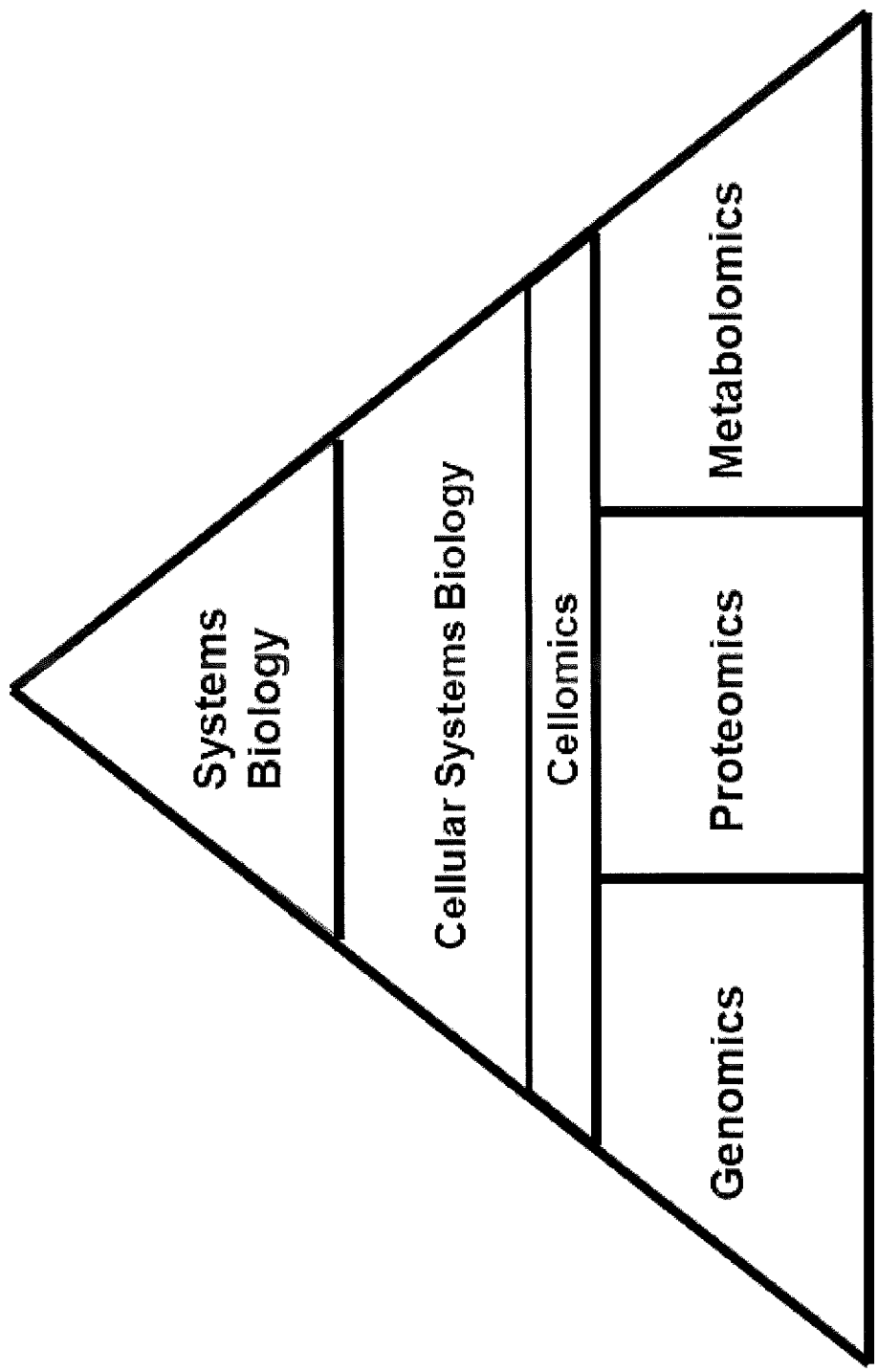
FIG. 3 is a schematic illustrating the interrelation of systems cell biology which captures enough complexity to correlate biomarkers with higher level organ and organism effects, while allowing high throughput and cost-effective profiling. Cellular systems biology and systems biology are based on the interactions and relationships between the fundamental components of living systems represented by the "-omics" and a selection of specific cellular biomarkers are obtained from a combination of genomics, proteomics and metabolomics, in the context of the cells studied (cellomics).
Figure 4:
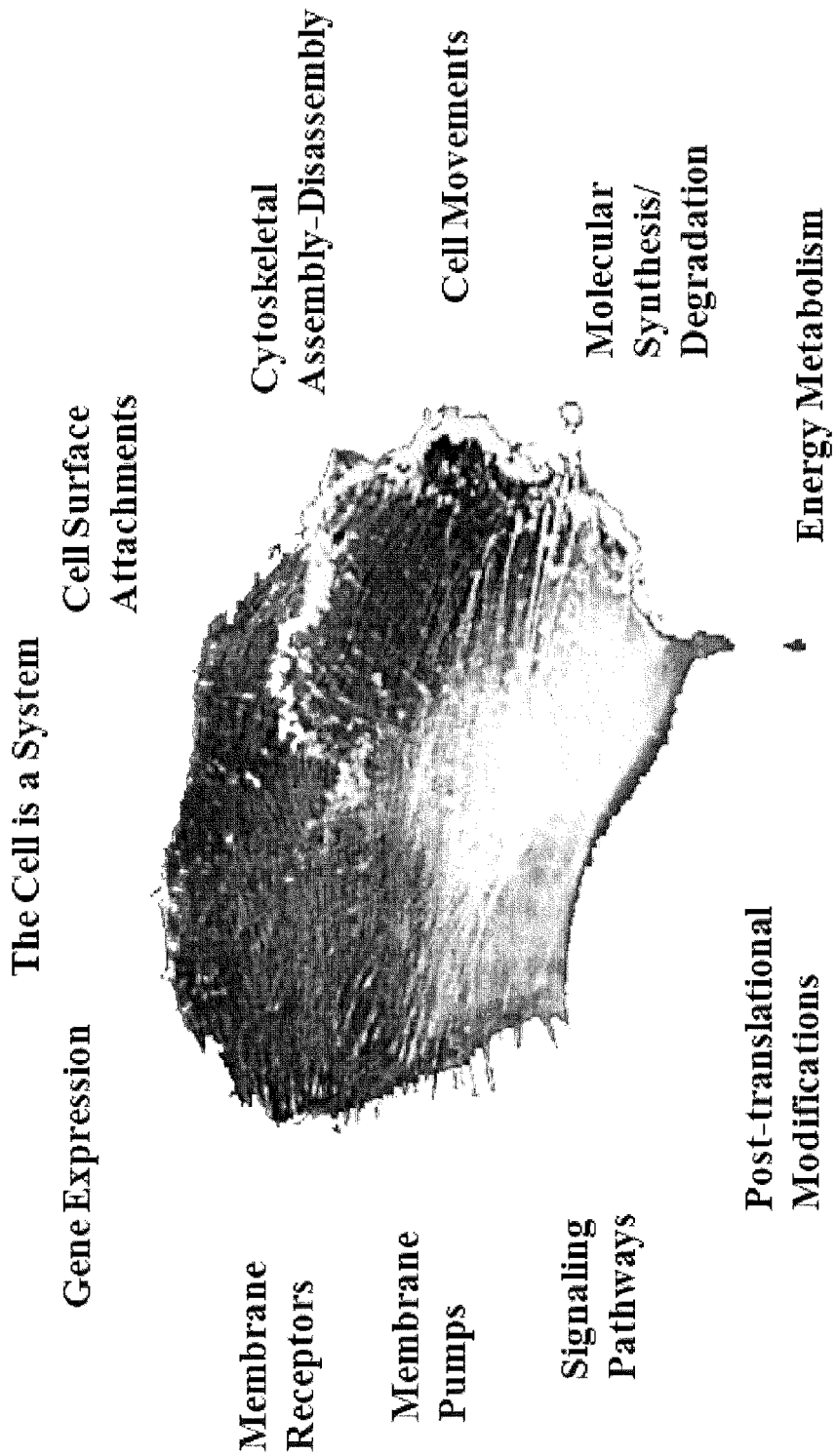
FIG. 4 is a schematic of how a cell integrates the many processes illustrated, such as gene expression, energy metabolism, etc. to yield normal functions. Diseases result from the dysregulation of one or more of these cellular processes which often results in complex symptoms. Many of these processes share pathways, signals and proteins and therefore should be investigated as part of the cell system (including the collection of cells of different types in tissues).

"Cellular systems biology" is defined as the investigation of the integrated and interacting networks of genes, proteins, and metabolic reactions that give rise to function and life. Cells in tissues, as complex systems, exhibit properties that are not anticipated from the analysis of individual components, known as emergent properties that require analysis of many factors to characterize cellular states. Taylor and Giuliano [10] describe the application of in vitro cell systems analysis to drug discovery. In this analysis, correlation between measurements in individual cells was required to identify and interpret cell responses to drug treatment.

"Cellular systems biology features" are defined as a data measurements or a series of measurements of a particular biological function (typically evidenced by the presence, absence and/or level of one or more biomarkers) made in time and/or space within cells and tissues. Examples of biological functions include, but are not limited to: protein posttranslational modifications such as phosphorylation, proteolytic cleavage, methylation, myristoylation, and attachment of carbohydrates; translocations of ions, metabolites, and macromolecules between compartments within or between cells; changes in the structure and activity of organelles; and alterations in the expression levels of macromolecules such as coding and non-coding RNAs and proteins.

Cellular Systems Biology analysis of cells in tissues makes use of some of the cell analysis algorithms developed for High Content Screening (HCS). "HCS" is defined as a technology platform designed to measure the temporal and spatial activities of genes, proteins, and other cellular constituents in living cells in response to drug treatment (Giuliano, K. A.; Haskins, J. R.; Taylor, D. L., Advances in high content screening for drug discovery. *ASSAY and Drug Development Technologies* 2003, 1, 565-577). HCS and multiparameter HCS were developed to measure individual targets or pathways in arrays of cultured cells in response to drug treatment. However, as described herein, HCS image analysis tools can also be used to extract data from cells in tissues as part of a cellular systems biology profiling approach that would enable the characterization of complex and emergent properties that arise in living cells and tissue. In addition, numerous other image analysis software packages, including those that are supplied with microscope slide scanning systems could be applied to extract cellular features from images of tissues to build a cellular systems biology profile.

"Cellular systems biology profiles" are defined as the interrelationships between combination of at least about five cellular systems biology features collected from cells within one or more tissue sections from the same sample. These interrelationships are calculated either arithmetically (e.g., ratios, sums, or differences between cellular systems biology feature values) or statistically (e.g., hierarchical clustering methods or principal component analyses of combinations of cellular systems biology feature values). Cellular systems biology profiles can be used to understand the complex response of cells and tissues to disease and various treatments by characterizing the emergent properties of the cellular systems response.

"Emergent properties" refers to the arising of novel and coherent structures, patterns, and properties during the process of self-organization in complex systems (Goldstein, Jeffrey (1999), "Emergence as a Construct: History and Issues", *Emergence: Complexity and Organization* 1: 49-72). The emergent properties of cells and tissues (e.g., growth and division, transformation to a tumor phenotype, etc.) cannot begin to be defined until a systemic analysis of complex cellular function is undertaken. Emergent properties are not anticipated from the analysis of individual components, but require analysis of many factors to characterize cellular states.

Although the analysis of single, individual features in tissue sections has value, the application of a "systems approach" wherein, as provided herein, multiple features (e.g., at least about four features, at least about five features, at least about six features, at least about 7-12 features, or more), of a tissue are analyzed, enables a more precise determination of the state of the cells, the tissues, and the organism as a whole. Furthermore, this approach facilitates, for example, the automation of tissue analysis, and the production of tissue profiles for more precise tumor staging, personalized treatments, evaluation of treatment efficacy, and early indication of side effects, as well as improved analyses in animal toxicology studies in drug discovery.

Systems Biology and Cellular Systems Biology: The cell is the simplest living system. Tissues are collections of specific cell types forming interacting colonies of cells. Although cells and tissues are less complex than a complete organism, they possess significant functional complexity allowing a detailed understanding of the cellular basis of disease, treatment efficacy and potential toxicity of treatments. Multicolor fluorescence of multiplexed biomarkers coupled with searchable databases provides the basis for systems cell analysis.

Prior to this invention, the analysis and profiling of tissue-based cellular systems biology has not been described. The cellular systems biology approach, including the combining of traditional histological staining with fluorescent staining to associate cellular and tissue markers that can be labeled by fluorescence has not been previously done by others as now described herein. The use of the transmitted light images based on traditional (non-fluorescent) histological stains used by pathologist as a "reference" image or "map" for better interpretation of the multiple fluorescence-based reagents as described herein will increase the acceptance of the systems approach by pathologists and will allow the selection of a specific set of biomarkers for fluorescence analysis.

In one embodiment of the invention, provided is a method for producing a cellular systems biology profile of one or more tissue samples. As used herein, "cellular systems biology" (also referred to herein as systems cell biology), is the investigation of the integrated and interacting networks of genes, proteins, and metabolites that are responsible for normal and abnormal cell functions. Thus, a cellular systems biology profile is a systemic characterization of cells in the context of a tissue architecture such that the cells have particular characteristics dependent upon the relationships of different cells within a tissue and the biological or medical state of the tissue. It is the interactions, relationships, and state of the constituents of cells within a tissue that gives rise to the cellular systems biology features that are used to construct a profile. The interrelationships within a cellular systems biology profile are defined or calculated, for example, either arithmetically (e.g., ratios, sums, or differences between cellular systems biology feature values) or statistically (e.g., hierarchical clustering methods or principal component analyses of combinations of cellular systems biology feature values). In a particular embodiment, a cellular systems biology profile defines the interrelationships between a combination of at least about five cellular systems biology features collected from cells within one or more tissue sections from the same sample. In another embodiment, a cellular systems biology profile is the combination of at least about six, seven, eight, nine, ten, eleven, twelve, or more features.

In one embodiment of the invention, the method comprises obtaining at least two sections from one or more tissue samples. Any suitable tissue sample can be used in the methods described herein. For example, the tissue can be epithelium, muscle, organ tissue, nerve tissue, tumor tissue, and combinations thereof. In one embodiment, blood is not a tissue sample. Samples of tissue can be obtained by any standard means (e.g., biopsy, core puncture, dissection, and the like, as will be appreciated by a person of skill in the art). At least one section is labeled with a histological stain, to produce a histologically stained section. As used in the invention described herein, histological stains can be any standard stain as appreciated in the art, including but not limited to, alcian blue, Fuchsin, haematoxylin and eosin (H&E), Masson trichrome, toluidine blue, Wright's/Giemsa stain, and combinations thereof. As will be appreciated by a person of skill in the art, traditional histological stains are not fluorescent. At least one other section is labeled with a panel of fluorescently labeled reagents to produce a fluorescently labeled section. As used in the invention described herein, the panel of fluorescently labeled reagents comprises a number of reagents, such as fluorescently labeled antibodies, fluorescently labeled peptides, fluorescently labeled polypeptides, fluorescently labeled aptamers, fluorescently labeled oligonucleotides (e.g. nucleic acid probes, DNA, RNA, cDNA, PNA, and the like), fluorescently labeled chemicals and fluorescent chemicals (e.g., Hoechst 33342, propidium iodide, Draq-5, Nile Red, fluorescently labeled phalloidin), and combinations thereof. Each fluorescently labeled reagent is specific for at least one biomarker. As used herein, a "biomarker" is a molecule which provides a measure of cellular and/or tissue function. For example, and without limitation, a biomarker can be the measure of receptor expression levels, (e.g., estrogen receptor expression levels, Her2/neu expression); transcription factor activation; location or amount or activity of a protein, polynucleotide, organelle, and the like; the phosphorylation status of a protein, etc. In one embodiment, a biomarker is a nucleic acid (e.g., DNA, RNA, including micro RNAs, snRNAs, mRNA, rRNA, etc.), a receptor, a cell membrane antigen, an intracellular antigen, and extracellular antigen, a signaling molecule, a protein, and the like. In one embodiment of the invention, the panel of fluorescently labeled reagents detects at least about four different biomarkers. In another embodiment of the invention, the panel of fluorescently labeled reagents detects at least about four to about six, to about ten, to about twelve different biomarkers or more. In another embodiment of the invention, the panel of fluorescently labeled reagents detects at least about three different biomarkers. In a further embodiment, each fluorescently labeled reagent has different fluorescent properties, which are sufficient to distinguish the different fluorescently labeled reagents in the panel.

The detection of a biomarker in one or more sections is a read-out of one or more features of a cellular systems biology profile. As used herein, a "feature" is a characteristic which provides a measurement or series of measurements of a particular biomarker (which can indicate a biological function) made in time and/or space within cells and tissues. Biological functions include, but are not limited to: protein posttranslational modifications such as phosphorylation, proteolytic cleavage, methylation, myristoylation, and attachment of carbohydrates; translocations of ions, metabolites, and macromolecules between compartments within or between cells; changes in the structure and activity of organelles; and alterations in the expression levels of macromolecules such as coding and non-coding RNAs and proteins, morphology, state of differentiation, and the like. A single biomarker can provide a read-out of more than one feature. For example, Hoechst dye detects DNA, which is an example of a biomarker. A number of features can be identified by the Hoechst dye in the tissue sample such as nucleus size, cell cycle stage, number of nuclei, presence of apoptotic nuclei, etc.

The method further comprises imaging the histologically stained section using a first optical mode, which produces a first set of data and imaging the fluorescently labeled section using a second optical mode, which produces a second set of data. As will be appreciated by the person of skill in the art, as used in the invention described herein, the optical mode for imaging can be any mode suitable for this use, e.g., transmitted light microscopy, fluorescence light microscopy, wide field microscopy, confocal microscopy, and combinations thereof, as appropriate. In one embodiment, the data produced in either or both of the first set of data and second set of data can be digital data. The first set of data and the second set of data are analyzed to identify five or more features, such that at least one feature is identified in the first set of data and at least one feature is identified in the second set of data. The combination of the five or more features generates a cellular systems biology profile of the one or more tissue samples.

In one embodiment of the invention, the imaging procedures are automated. Furthermore, analyzing the data can be performed manually, by automation or a combination thereof. As will be appreciated by a person of skill in the art, imaging a histologically stained section and imaging a fluorescently labeled section can be done sequentially or simultaneously. In addition, histological labeling and fluorescent labeling can be done sequentially or simultaneously. In some embodiments, after obtaining one or more sections from a tissue sample, the method is wholly automated.

In a further embodiment of the invention, the method further comprises comparing the cellular systems biology profiles of two or more tissue samples in order to identify similarities, differences, or combinations thereof, of the two or more tissue samples. In one embodiment, the two or more tissue samples are serial sections from a single tissue specimen. Serial sections of a single tissue sample are tissue sections which were adjacent to each other in the preparation of two or more sections from a tissue sample.

In one embodiment of the invention, the one or more tissue samples are isolated from one or more animals. For example, in one embodiment, the one or more animals are one or more humans. In a particular embodiment, one or more tissue samples are isolated from a human patient at one or more time points, such that at least one tissue sample is isolated from each time point from the same patient.

In another embodiment of the invention, the panel of fluorescently labeled reagents indicate the presence, amount, location, activity, distribution, or combination thereof, of the biomarkers in the fluorescently labeled section. The location of a biomarker can be intracellular, extracellular, within specific intracellular locations, at specific extracellular locations, and combinations thereof. Activity of a biomarker can be the activation state of the biomarker (such as indicated, e.g., by its phosphorylation state, conformation state, or intracellular location, and the like).

In a further embodiment of the invention, the cellular systems biology profile is stored in a database for reference, thereby providing a reference cellular systems biology profile in a database. In one embodiment, the database is a computer. In another embodiment, the database is stored on a server. In one embodiment, the reference cellular systems biology profile in the database is compared with a cellular systems biology profile of one or more further samples. This permits the identification of similarities, differences, or a combination thereof, of the cellular systems biology profile of the one or more further samples and the reference cellular systems biology profile. Various methods can be used to compare the cellular systems biology profile of the one or more further samples and the cellular systems biology profile in the database, such as by graphical display, cluster analysis, or statistical measure of correlation and combinations thereof.

In a further embodiment of the invention, the method for producing a cellular systems biology profile of one or more tissue samples further comprises producing a cellular systems biology profile of at least one blood sample obtained from the same source as the one or more tissue samples. In one embodiment, the blood sample is a peripheral blood sample. Peripheral blood is the cellular components of blood, consisting of red blood cells, white blood cells, and platelets, which are found within the circulating pool of blood and not sequestered within the lymphatic system, spleen, liver, or bone marrow. The method comprises obtaining at least one blood sample smear from at least one peripheral blood sample from the same source as the one or more tissue samples. As used in the invention described herein, peripheral blood samples can be obtained by any standard procedure. The at least one blood sample smear is labeled with a panel of fluorescently labeled reagents to produce a fluorescently labeled blood sample smear, wherein each fluorescently labeled reagent is specific for a biomarker. In one embodiment, the panel of fluorescently labeled reagents detects at least about four different biomarkers. The detection of a biomarker is a read-out of one or more features of a cellular systems biology profile. The method further comprises imaging the fluorescently labeled blood sample smear with at least a third optical mode, such that the imaging produces a third set of data. The third set of data is analyzed to identify at least about five or more features, wherein the five or more features is a cellular systems biology profile of the at least one blood sample smear. This method produces a cellular systems biology profile of the at least one peripheral blood sample obtained from the same source as the one or more tissue samples. In one embodiment, the at least one peripheral blood sample is taken at the same or different time point as the one or more tissue samples are obtained. In another embodiment, more than one peripheral blood sample is taken at different time points, and the cellular systems biology profiles of the more than one peripheral blood samples are compared.

In another embodiment of the invention, the method for producing a cellular systems biology profile of one or more tissue samples further comprises producing a cellular systems biology profile of one or more peripheral blood samples obtained from the same source as the one or more tissue samples. The method comprises obtaining at least two blood sample smears from one or more peripheral blood samples. At least one blood sample smear is labeled with a histological stain to produce a histologically stained blood sample smear. In addition, at least one blood sample smear is labeled with a panel of fluorescently labeled reagents to produce a fluorescently labeled blood sample smear. Each fluorescently labeled reagent is specific for a biomarker, and wherein the panel of fluorescently labeled reagents detects at least about four different biomarkers, and wherein the detection of a biomarker is a read-out of one or more features of a cellular systems biology profile. The histologically stained blood sample smear is imaged with at least a third optical mode to produce a third set of data. The fluorescently labeled blood sample smear is imaged with at least a fourth optical mode to produce a fourth set of data. The third set of data and the fourth set of data are analyzed to identify at least about five or more features, wherein at least one feature is identified in each of the third set of data and the fourth set of data, such that the combination of the five or more features is a cellular systems biology profile of the one or more blood sample smears. Thus the method produces a cellular systems biology profile of the one or more peripheral blood samples obtained from the same source as the one or more tissue samples. As discussed above, in one embodiment, the one or more peripheral blood samples are taken at the same or different time point as the one or more tissue samples are obtained. Furthermore, in another embodiment, when one or more peripheral blood samples are taken at different time points, the cellular systems biology profiles of the one or more peripheral blood samples are compared.

In an additional embodiment of the invention, provided herein is a method for producing a cellular systems biology profile of one or more tissue samples. The method comprises obtaining at least one section from one or more tissue samples. At least one section is labeled with a panel of fluorescently labeled reagents to produce a fluorescently labeled section, such that each fluorescently labeled reagent is specific for a biomarker. In one embodiment, the panel of fluorescently labeled reagents detects at least about four different biomarkers, and the detection of a biomarker is a read-out of one or more features of a cellular systems biology profile. The method further comprises imaging the fluorescently labeled section with at least a first optical mode to produce a first set of data which is analyzed to identify at least about five or more features, wherein at least one feature is identified in the first set of data, and wherein the combination of the five or more features is a cellular systems biology profile the one or more tissue samples. Thus, the method produces a cellular systems biology profile of the one or more tissue samples. In a further embodiment, the method further comprises producing a cellular systems biology profile of at least one peripheral blood sample obtained from the same source as the one or more tissue samples. The method comprises obtaining at least one blood sample smear from at least one peripheral blood sample. The at least one blood sample smear is labeled with a panel of fluorescently labeled reagents to produce a fluorescently labeled blood sample smear, such that each fluorescently labeled reagent is specific for a biomarker. The panel of fluorescently labeled reagents detects at least about four different biomarkers, and the detection of a biomarker is a read-out of one or more features of a cellular systems biology profile. The method further comprises imaging the fluorescently labeled blood sample smear with at least a second optical mode to produce a second set of data. The second set of data is analyzed to identify at least about five or more features, such that the five or more features is a cellular systems biology profile of the at least one blood sample smear. Thus, the method produces a cellular systems biology profile of the at least one peripheral blood sample obtained from the same source as the one or more tissue samples. In an optional embodiment, the method further comprises labeling at least one blood sample smear with a histological stain to produce a histologically stained blood sample smear. The histologically stained blood sample smear is imaged to produce an additional set of data which is analyzed to identify at least one feature, wherein the combination of the five or more features identified in the combination of the histologically stained blood sample smear and the fluorescently stained blood sample smear is a cellular systems biology profile of the one or more blood sample smears.

In a further embodiment of the invention, provided herein is a method for producing a cellular systems biology profile of one or more tissue samples, wherein the tissue sample is profiled for the presence of cancer, the stage of a cancer, the diagnosis of a cancer, the prognosis of a cancer and/or the absence of a cancer. As will be understood by a person of skill in the art, different cancers can be classified and staged according to their pathology. The method described herein permits, for example, the confirmation of the presence or absence of a cancer, the identification of a cancer, the classification of a cancer stage, the prediction and/or determination of the outcome or prognosis of the cancer, and the response of the cancer to any treatments. The method comprises obtaining at least two sections from one or more tissue samples. At least one section is labeled with a histological stain to produce a histologically stained section. At least one section is labeled with a panel of fluorescently labeled reagents to produce a fluorescently labeled section. Each fluorescently labeled reagent is specific for a biomarker. The panel of fluorescently labeled reagents comprises fluorescently labeled reagents which can be selected from the group consisting of: i) a set of fluorescently labeled reagents specific for at least four cancer cell biomarkers; ii) a set of fluorescently labeled reagents specific for at least four migratory immune cell biomarkers; iii) a combination of A) a set of fluorescently labeled reagents specific for at least three cancer cell biomarkers and B) a set of fluorescently labeled reagents specific for at least three migratory immune cell biomarkers, and iv) combinations of the above, such that the panel of fluorescently labeled reagents detects at least about four different biomarkers. The detection of a biomarker is a read-out of one or more features of a cellular systems biology profile. The method further comprises imaging the histologically stained section with at least a first optical mode to produce a first set of data and imaging the fluorescently labeled section with at least a second optical mode to produce a second set of data. The first set of data and second set of data are analyzed to identify at least about five or more features, such that at least one feature is identified in each of the first set of data and the second set of data. The combination of the five or more features is a cellular systems biology profile of the one or more tissue samples, and thus the method produces a cellular systems biology profile of the one or more tissue samples, wherein the tissue sample is profiled for the presence of a cancer, the stage of a cancer, the diagnosis of a cancer, the prognosis of a cancer or the absence of a cancer. In one embodiment, the cancer is breast cancer.

In a further embodiment, the fluorescently labeled reagents specific for cancer cell biomarkers detect cancer cell markers such as HER2/neu, estrogen receptor (ER), Ki-67, Cox-2, p16 and the like. In another embodiment, the fluorescently labeled reagents specific for migratory immune cell biomarkers detect migratory immune cell biomarkers such as NK cell biomarkers, LAK cell biomarkers, TRAIL, PD1, biomarkers of immune cell apoptosis, and the like. In an additional embodiment, a feature is a ratio of different migratory immune cell subtypes as detected by the migratory immune cell biomarkers, such that the ratio is indicative of the presence of a cancer, the stage of cancer, the diagnosis of a cancer, the prognosis of a cancer, the absence of a cancer and combinations thereof.

In a further embodiment, the one or more tissue samples is selected from the group consisting a suspected or known cancerous tissue, a lymph node, and a combination thereof.

Migratory immune cells are typically white blood cells (leukocytes). In one embodiment, examples of migratory immune cell biomarkers include, without limitation, the percentage and ratios of specific migratory immune cells in tumors, tumor draining lymph nodes, non-sentinel lymph nodes and peripheral blood. Examples of migratory immune cells in normal blood include: (1) lymphocytes (25% of white blood cells) which includes T-cells (distinct sub-types), B-cells (distinct sub-types), and natural killer (NK) cells; (2) Neutrophils (65% of white blood cells); (3) Eosinophils (4% of white blood cells) and (4) Monocytes (6% of white blood cells), which includes macrophages (distinct sub-types). In one embodiment, the percentage ranges of immune cells in tissues for cellular systems biology profiling comprise one or more of the following: lymphocytes from about 1% to about 90% (with distinct sub-types within this percentage, as will be recognized by a person of skill in the art); neutrophils from about 1% to about 90%; eosinophils from about 0.01% to about 50%; monocytes from about 0.01% to about 50% (with distinct sub-types within this percentage, as will be recognized by a person of skill in the art). In another embodiment of the invention, the ranges of ratios of immune cells in tissues for cellular systems biology profiling comprise one or more of the following: T-cell lymphocytes/B-cell lymphocytes from about 0.1 to about 1000; dendritic cells/lymphocytes from about 0.01 to about 1000; macrophages/lymphocytes from about 0.01 to about 1000; lymphocyte sub-set/lymphocyte sub-set from about 0.01 to about 1000.

In a still further embodiment of the invention, the method for producing a cellular systems biology profile of one or more tissue samples, wherein the tissue sample is profiled for the presence of cancer, the stage of a cancer, the diagnosis of a cancer, the prognosis of a cancer and/or the absence of a cancer further comprises producing a cellular systems biology profile of at least one peripheral blood sample obtained from the same source as the one or more tissue samples. The method comprises obtaining at least one blood sample smear from at least one peripheral blood sample and labeling the at least one blood sample smear with a panel of fluorescently labeled reagents to produce a fluorescently labeled blood sample smear. Each fluorescently labeled reagent is specific for a biomarker, and the panel of fluorescently labeled reagents detects at least about four different biomarkers. The detection of a biomarker is a read-out of one or more features of a cellular systems biology profile. The method further comprises imaging the fluorescently labeled blood sample smear with at least a third optical mode to produce a third set of data. The third set of data is analyzed to identify five or more features, wherein the five or more features is a cellular systems biology profile of the at least one blood sample smear. Thus, the method produces a cellular systems biology profile of the at least one peripheral blood sample obtained from the same source as the one or more tissue samples. In one embodiment, the at least one peripheral blood sample is taken at the same or different time point as the one or more tissue samples are obtained. In another embodiment, more than one peripheral blood sample is taken at different time points, and the cellular systems biology profiles of the more than one peripheral blood samples are compared.

In a still further embodiment of the invention, the method for producing a cellular systems biology profile of one or more tissue samples, wherein the tissue sample is profiled for the presence of cancer, the stage of a cancer, the diagnosis of a cancer, the prognosis of a cancer and/or the absence of a cancer further comprises producing a cellular systems biology profile of at least one peripheral blood sample obtained from the same source as the one or more tissue samples. The method comprises obtaining at least two blood sample smears from one or more peripheral blood samples and labeling at least one blood sample smear with a histological stain to produce a histologically stained blood sample smear. The method further comprises labeling at least one blood sample smear with a panel of fluorescently labeled reagents to produce a fluorescently labeled blood sample smear, such that each fluorescently labeled reagent is specific for a biomarker. The panel of fluorescently labeled reagents detects at least about four different biomarkers, and the detection of a biomarker is a read-out of one or more features of a cellular systems biology profile. The method also comprises imaging the histologically stained blood sample smear with at least a third optical mode to produce a third set of data and imaging the fluorescently labeled blood sample smear with at least a fourth optical mode to produce a fourth set of data. The third set of data and the fourth set of data are analyzed to identify at least about five or more features, wherein at least one feature is identified in each of the third set of data and the fourth set of data, such that the combination of the five or more features is a cellular systems biology profile of the one or more blood sample smears. Thus, the method produces a cellular systems biology profile of one the or more peripheral blood samples obtained from the same source as the one or more tissue samples, wherein the tissue sample is profiled for the presence or absence of a cancer, the stage of a cancer, the diagnosis of a cancer, the prognosis of a cancer of the absence of a cancer. In one embodiment, the one or more peripheral blood samples are taken at the same or different time points as the one or more tissue samples are obtained. In another embodiment, more than one peripheral blood samples are taken at different time points, and the cellular systems biology profile of the more than one peripheral blood samples are compared.

In another embodiment of the invention, provided herein is a method for producing a cellular systems biology profile of one or more tissue samples, wherein the tissue sample is profiled for the presence, severity or absence of a tissue toxicity. The method comprises obtaining at least two sections from one or more tissue samples. At least one section labeled with a histological stain to produce a histologically stained section and at least one section is with a panel of fluorescently labeled reagents to produce a fluorescently labeled section. Each fluorescently labeled reagent is specific for a biomarker. The panel of fluorescently labeled reagents comprises a set of fluorescently labeled reagents selected from the group consisting of i) a set of fluorescently labeled reagents specific for cell metabolism biomarkers, ii) a set of fluorescently labeled reagents specific for DNA damage biomarkers, iii) a set of fluorescently labeled reagents specific for cell morphology biomarkers, iv) a set of fluorescently labeled reagents specific for DNA damage biomarkers, v) a set of fluorescently labeled reagents specific for cell differentiation biomarkers, vi) a set of fluorescently labeled reagents specific for stress-induced transcription activation or inhibition biomarkers, vii) a set of fluorescently labeled reagents specific for phosphorylation status of stress kinase biomarkers, viii) a set of fluorescently labeled reagents specific for apoptosis or necrosis biomarkers, ix) a set of fluorescently labeled reagents specific for cytoskeleton biomarkers, x) a set of fluorescently labeled reagents specific for organelle biomarkers, xi) a set of fluo- rescently labeled reagents specific for presence or activation of immune cell biomarkers, and xii) combinations thereof, such that the panel of fluorescently labeled reagents detects at least about four different biomarkers, and wherein the detection of a biomarker is a read-out of one or more features of a cellular systems biology profile. The histologically stained section is imaged with at least a first optical mode to produce a first set of data. The fluorescently labeled section is imaged with at least a second optical mode to produce a second set of data. The method further comprises analyzing the first set of data and second set of data to identify at least about five or more features, wherein at least one feature is identified in each of the first set of data and the second set of data. The combination of the five or more features is a cellular systems biology profile of the one or more tissue samples. Thus, the method produces a cellular systems biology profile of the one or more tissue samples, wherein the tissue sample is profiled for the presence, severity or absence of a tissue toxicity. In one embodiment, the one or more tissue samples is one or more liver tissue samples.

As will be understood by a person of skill in the art, the methods of the invention as described herein can be used in many applications. The invention advances technologies currently in practice, some of which are outlined herein.

Staining and Transmitted Light Imaging in Pathology, Toxicology and Personalized Medicine: Standard histological methods for staining and imaging of tissue sections in Pathology, and Toxicology were developed to meet the needs of pathologists and toxicologists to view the sections and make a determination based on experience and knowledge. Stains such as H&E (Hematoxylin and Eosin), congo red, Gram bacterial stain and others provide the means to label various cell types and structures, to facilitate interpretation. Although experienced pathologists can learn to interpret the staining patterns, efforts to automate the interpretation of the patterns have met with great difficulty. Fluorescent labeling technologies, especially when coupled with antibodies or other molecularly specific biomarkers or tags such as aptamers, allow for very specific labeling of cellular components, high signal to background, the ability to distinguish multiple labels on a single specimen, and the ability to detect comparatively small numbers of targets in each cell. While these properties make fluorescence nearly ideal for automated imaging, the use of fluorescence in visual interpretation is more limited due to bleaching, limited spectral response of the eye, and the limited dynamic range of the eye. Efforts to automate pathology have principally been guided by the staining and interpretation methods used by the pathologist.

Software tools have been developed to automate the acquisition, and management of images from tissue sections. For example, the Bacus Laboratories, Inc. (Chicago, Ill.) has developed software to analyze transmitted light tissue sections and tissue arrays along with software tools for image sharing and remote analysis.

Drug Discovery: On average, pharmaceutical companies spend more than $1 billion to bring a new drug to market, yet despite this large investment of time and resources, the frequency of drug failure is high. Poor efficacy and drug induced toxicity continue to be major causes of these failures [11, 12]. Furthermore, many candidate drugs fail late, in animal testing or clinical testing, after significant investment in development. Clearly, improved methods of functional assessment are needed in drug discovery, as well as in other fields such as environmental health and industrial safety. Efficacy and toxicity studies are carried out at several points during drug development including cell-based assays, ADME animal studies and clinical trials. Improvements in the reliability of tissue analysis are expected to improve the reliability and safety of drug testing.

Personalized medicine: Genomics and proteomics have laid the groundwork for diagnostic and therapeutic treatments that are customized for each individual patient. This personalized medicine is based on a systems approach to disease which takes into account a profile of the whole patient, to determine the most effective therapy [2]. The molecular information derived from genomics and proteomics, and in particular those genes and proteins that have been correlated with particular disease conditions, often referred to as biomarkers, is certainly a valuable source of patient data, but the customization of the treatments will still be limited to well characterized classes of biomarkers, since therapies cannot be tested for every individual genome.

Environmental Toxicology: The challenge in environmental toxicology is to assess the impact of a growing list of natural and man-made substances on human health. Several factors complicate the problem: increasing large numbers of substances must be tested; the complexities of environmental exposure require testing over a broad range of exposure mechanism, concentration and time; and uncertainties regarding the influence of age and genetic variability on the results. Reliable means to improve the efficiency of testing and evaluation are actively being sought by the National Toxicology Program at the National Institutes of Health.

Biomedical research: Cell analysis is routinely used in basic biological research as well as in medical research. In both cases the cell analysis is usually focused on a single cellular process, as there are limited tools available for analyzing complex, multi-component system responses.

Systems biology is an emerging research field focused on the interactions between system components and pathways.

Functional Assessment: In vivo toxicology measures acute and chronic toxicity in several areas including mutagenicity, organ cytotoxicity, immunotoxicity, neurotoxicity, teratogenicity, and safety pharmacology. In vitro toxicology assays, such as CYP450 induction, Ames test, MTT assay and others, are used to measure these functional responses. In vitro toxicology assays are typically cell based assays which use a variety of cell types including hepatocytes, cardiomyocytes, and others.

Toxicogenomics uses a combination of traditional genetics and toxicology to identify patterns of gene expression that are associated with toxic effects. Toxicogenomics profiles typically include information such as nucleotide sequences, gene expression levels, protein synthesis, protein function and some phenotypic responses. One goal of toxicogenomics is to identify a sequence of genomic events that lead to a toxic biological response. [13].

Cell-Based Assays of Cytotoxicity: Existing cell based assays of cytotoxicity are designed to detect a specific endpoint in a population of cells. Examples include trypan blue staining, in which cell death is assessed microscopically by measuring the uptake of trypan blue dye that is excluded by live cells. Other vital stains and fluorescent DNA-binding dyes which are also excluded from live cells can also be used. In another assay format, live cells are labeled with a probe which is released upon cell death. Toxicity can also be assessed by measuring specific cellular functions. One of the more common assays is the MTT assay, where cell proliferation is measured by the activity of a mitochondrial enzyme. Other assays measure specific cellular markers. Examples include measurement of the activation of markers associated with the inflammation such as PGE-2, TNFα, IL1b and other interleukins. Assay formats can be in live cells, fixed cells or cell extracts. Many of the same biomarkers used in these assays will be useful as components of a panel of tissue based cellular biomarkers.

Metabolism: Drug effect on metabolism is measured by radioactive precursor uptake, thymidine, uridine (or uracil for bacteria), and amino acid, into DNA, RNA and proteins. Carbohydrate or lipid synthesis is similarly measured using suitable precursors. Turnover of nucleic acid or protein, or the degradation of specific cell components, is measured by prelabeling (or pulse labeling) followed by a purification step and quantitation of remaining label or sometimes by measurement of chemical amounts of the component. Energy source metabolism is also analyzed for optimal cell growth.

Light microscopy shows the general state of cells, and combined with trypan blue exclusion, the percent of viable cells. Small, optically dense cells indicate necrosis, while bloated "blasting" cells with blebs indicate apoptosis. Phase microscopy views cells in indirect light; the reflected light shows more detail, particularly intracellular structures. Fluorescence microscopy detects individual components in cells, after labeling with selective dyes or specific antibodies, and can be used to identify cellular features associated with metabolic states.

High Content Screening: High Content Screening (HCS) was developed as a method whereby one or more cellular features are measured and analyzed in arrays of cells to identify a cellular functional response [5, 14, 15]. For example, an HCS assay might be used to measure the activation of a particular receptor [16], mitochondrial activity [17], the onset of apoptosis [5, 18], or another cellular function.

Each of these cellular features represents a measurement of particular cellular component. In some HCS assays a single cellular feature is sufficient to indicate a single cellular function or response. In other cases, the measurement of several features is required to specifically indicate a cellular response. For example, a commercial apoptosis assay uses four cell features to more specifically indicate apoptosis. These features are interpreted based on the knowledge of the biology of apoptosis.

Multiparameter cytotoxicity assays have been developed by nearly all vendors of HCS technologies. These assays are typically two to four parameter assays which measure cellular features related to cell death, either by necrosis or apoptosis. These assays have been applied in drug discovery, and testing for environmental agents of biowarfare [19] on cultured cells and primary cell preparations. Many of the biomarkers used in HCS can also be used in combinations as components of a feature vector of cellular states in tissue sections and other tissue specimens.

Reagent Technologies: Multiple reagent technologies are available to assay cellular functions. Fluorescent reagent technologies have matured over the last two decades, with probes available to label subcompartments, localize proteins, label membranes, respond to membrane potentials, sense the local chemical environment, read out molecular mobility, and provide many other measurements [20]. Coupled with antibodies, immunofluorescence labeling provides an easy method for detecting and localizing proteins or protein variants such as phosphorylated proteins. Cells can be engineered to express proteins tagged with any of the color variants of fluorescent proteins [21, 22], and these fluorescent proteins can be further engineered to create biosensors, indicators of specific cellular functions [16, 23-25]. A variety of labels can be combined in a single sample preparation to provide for the measurement of many features in each individual cell in a population, as well as in the population as a whole [10, 26]. Quantum dots, with their single excitation wavelength and narrow emission bands, provide the potential for even higher degrees of multiplexing within an assay [27]. In addition the rainbow of fluorescent probes, there are a number of bioluminescent and chemiluminescent reagents that can be effectively used in cell based assays [28, 29].

Multiparameter High Content Screening Profiles: A recent comparison of the performance of a panel of cytotoxicity assays, including DNA synthesis, protein synthesis, glutathione depletion, superoxide induction, Caspase-3 induction, membrane integrity and cell viability found that these assays on average had only half the predictive power of animal studies [11]. In contrast, a relatively simple four parameter high content screening assay using human hepatocytes was found to be more predictive than animal-based toxicity assays (O'Brien, P. J.; Irwin, W.; Diaz, D.; Howard-Cofield, E.; Krejsa, C. M.; Slaughter, M. R.; Gao, B.; Kaludercic, N.; Angeline, A.; Bernardi, P.; Brain, P.; Hougham, C., High concordance of drug-induced human hepatotoxicity with in vitro cytotoxicity measured in a novel cell-based model using high content screening. *Arch Toxicol* 80:580-604 (2006)).

However, these assays were carried out independently, analyzed only for lowest active concentration, and no attempt was made to combine the readouts in any quantitative way, to improve the overall predictivity. Several studies have shown that the multidimensional cellular responses from cell-based assays can be clustered using standard methods, to identify compounds with similar activities [10, 30, 31]. These studies have demonstrated proof of principle for clustering compound responses, but have not attempted to correlate these identified clusters with specific response profiles and then use the response to predict the physiological impact of unknown substances. Similarly, multidimensional characterization of cellular states in tissue or other specimens can be used to identify patterns of cellular states that are associated with specific disease conditions or patient responses to treatment.

Classification Tools: A simple automated classifier has been developed for use with some commercially available assays. This classifier allows the use of Boolean operations to combine the outputs from several assay features into a single result [32]. These Boolean operations allow the assay developer to define an output that combines several feature measurements. This is useful in expanding the scope of some HCS assays, but has limited features, and is certainly not designed for, nor would it be easy to use with multidimensional feature sets.

Multiplexed Fluorescence for Cellular Systems Biology Profiling of Patient Tissue Samples: The invention described herein is an improved method for characterizing patient tissue specimens based on the integration of specific fluorescence labeling technologies with image acquisition and image analysis to create tissue marker profiles. The invention also discloses the use of the profiles to classify tissue specimens for the purposes of identifying patient medical conditions, such as tumor staging and other disease states, as well as response to treatment.

One aspect of this invention is the integration of the use of traditional histological staining and transmitted light-based imaging with panels of molecularly specific, fluorescently labeled biomarkers to correlate morphometric interpretations with biomarker multiplexing in a "cellular systems biology profile." The outcome is a powerful machine-learning platform where the instrument is fast and the software is simple.

A number of instruments are available for transmitted light imaging of tissue sections. For example, the Hamamatsu (Bridgewater, N.J.) NanoZoomer instrument allows automated processing of many slides per day. A number of instruments are available for fluorescent imaging of slides, including confocal microscope, wide-field imaging, and HCS systems. Both wide-field imaging systems and HCS systems can further make use of software deconvolution or structured illumination methods to improve resolution of features in the sections. Therefore, both traditional and more powerful, molecularly specific fluorescent reporters can be imaged in tissue sections on slides or in microplates.

FIG. 3 illustrates the relationships between Systems Biology, Cellular systems biology, cellomics, Genomics, Proteomics and Metabolomics. Systems biology is the study of an organism, viewed as an integrated and interacting network of components, starting with genes, proteins, and biochemical pathways, that give rise to life. Because biological systems are complex, emergent properties result from interactions between system components. These emergent properties are properties that are not predicted from component properties, but are the result of interactions between components, and therefore require a systems approach to measurement and analysis.

Cellular systems biology is the study of the cell as the basic unit of life: an integrated and interacting network of genes, proteins and biochemical reactions which give rise to functions and life. The cell is the simplest functional biological system, and therefore an ideal system from which to extract knowledge about biological systems. Cellular systems biology involves the application of cellular analysis technologies to the understanding of how the interactions of cellular components gives rise to the complex biochemical and molecular processes that contribute to cell functions. These cell functions include complex behavioral responses of cells to environmental changes as well as experimental treatments. As illustrated in FIG. 3 Cellular systems biology is a component of Systems Biology.

The present invention relates to a method for identifying biological conditions in higher level organisms, including humans, from "systems-based" panel or panels of measurements of cellular and/or tissue features in tissue preparations, including blood, including sections, smears and other cellular tissue preparations. The "systems-based" panel of measurements within the same samples dramatically extends the present methodology that focuses on individual or a few parameters to the measurement and subsequent analysis of the systems response profile from the tissue investigated. The methods of this invention also provide a means to quantify the similarity of biological states and predicted modes of action based on the tissue system profiles. There are many applications which will benefit from the use of this invention, including animal testing in drug discovery and environmental health, medical diagnostics and human clinical trials. Application of this technology will improve the efficiency and reduce the cost of drug development. The invention will also improve the efficiency of environmental toxicology testing.

The invention includes various embodiments such as protocols, reagent panels, databases and informatics software.

Figure 5:
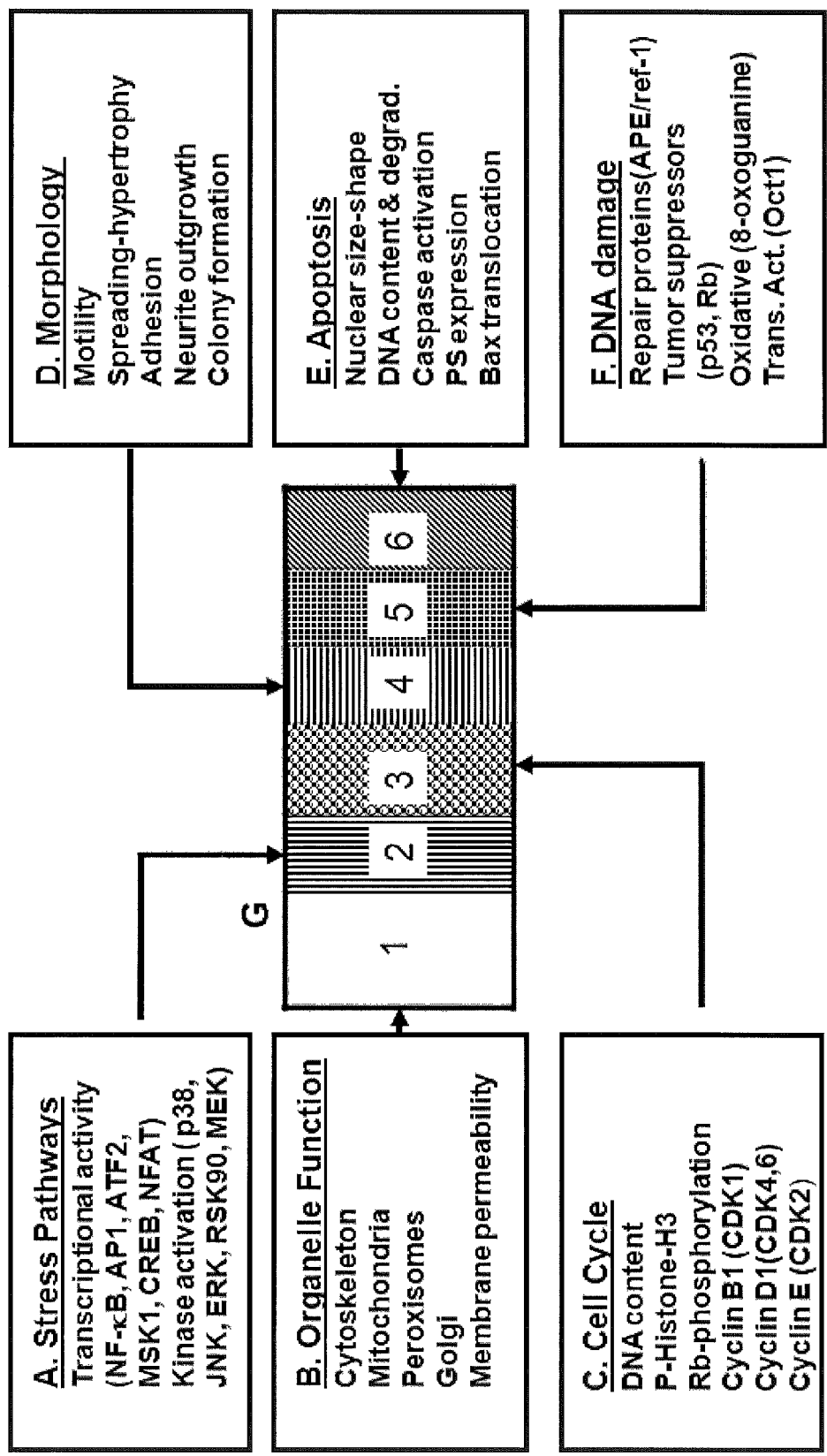
FIG. 5 illustrate examples of biomarkers for use in patient tissue profiling selected from function classes that include, for example: (A) Stress Pathways; (B) Organelle Function; (C) Cell Cycle; (D) Morphology; (E) Apoptosis; and (F) DNA Damage, as well as micro RNA, and migratory immune cells. Specific combinations of biomarkers are selected for analysis of particular disease conditions, as described herein.

FIG. 5 illustrates an example of an embodiment of the invention which comprises a panel of assay function classes used to profile toxicity. These function classes include Stress Pathways, Organelle Function, Cell Cycle Stage, Morphology Changes, Apoptosis and DNA Damage. Other function classes can be used in toxicity assessment and other functional applications of this method, as will be appreciated by a person of skill in the art. The methods of this invention can be used to validate additional assays and function classes which can be added to a profile to improve the sensitivity, specificity or range of applicability of a specific embodiment of this invention.

Figure 6:
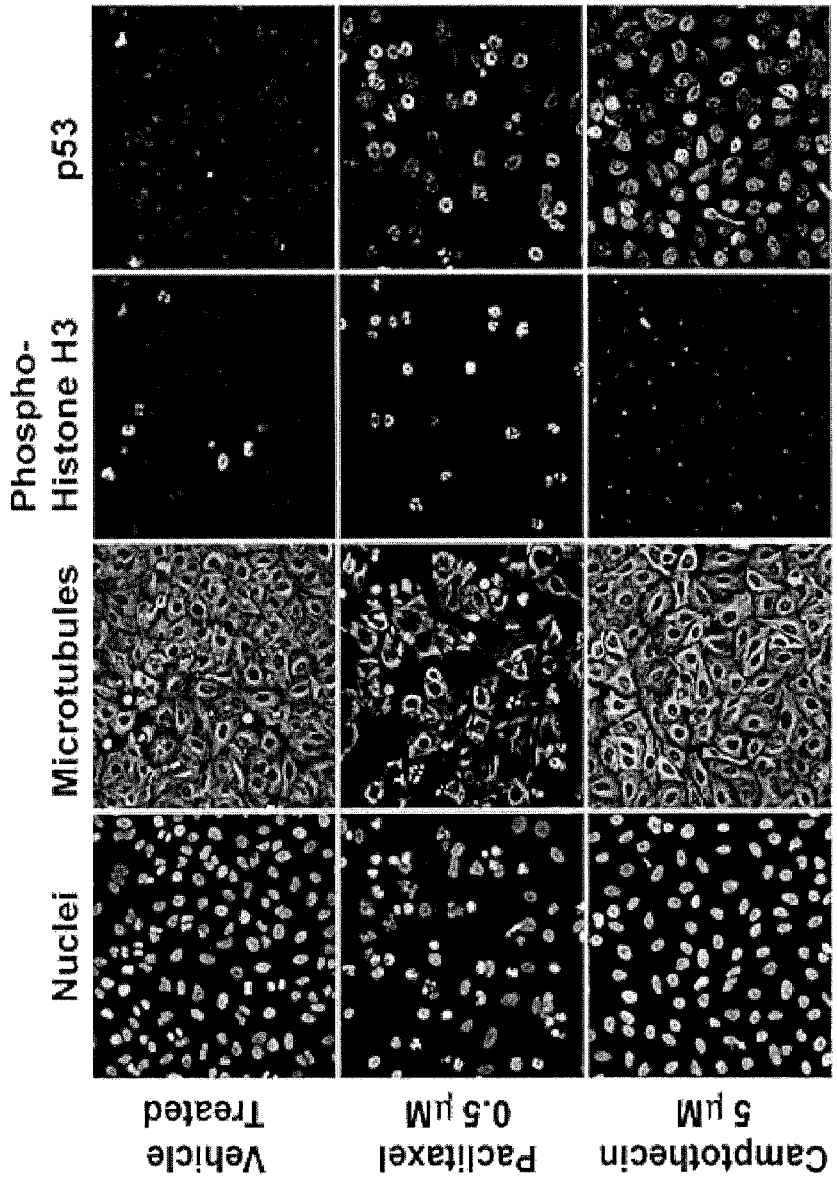
FIG. 6 is an example of the multiplexed labeling of cells with a panel of biomarkers such as would be used in tissue sections. Labels are multiplexed in tissue which allows analysis of correlations between biomarker activation within the same tissue, and to reduce the number of sections that must be prepared and analyzed. In a particular embodiment, at least four or more biomarkers are analyzed in each section.

Within each of these assay function classes, one or more assays are selected to be used to measure one or more cellular systems biology features of cells within a tissue as an indication of a response in that assay function class. To illustrate how cellular systems biology feature measurements can be made on cells or tissues, a similar high content screening assay with multiple features for cells in arrays is illustrated in FIG. 6. In this example assay, representative images from each channel of a multiplexed high content screen are shown. Algorithms are used to extract information from the images to produce outputs of at least four different cell features including nuclear size and shape, cell cycle distribution, DNA degradation, the state of the microtubule cytoskeleton, the activation state of the tumor suppressor p53, and the phosphorylation state of histone H3, a protein involved in the regulation of the cell cycle. Assays can be combined in two or more assay plates to produce a compound profile with six or more features. Assays such as this, which include image analysis algorithms with multiple output features are available from a variety of commercial sources, especially HCS technology vendors such as Cellomics (Pittsburgh, Pa.), GE Healthcare (Piscataway, N.J.), Molecular Devices (Sunnyvale, Calif.), and others, and can be implemented in any one of the standard image analysis software packages. The output features from the combination of assays, both commercial and custom developed, are combined to form a single response profile. In one embodiment, assays are selected from at least about four of the function classes in FIG. 5, to provide a sufficiently broad profile for predicting higher level integrated functions. One embodiment of this invention employs a panel of assays with one from each of these function classes. These assays are used first to build a predictive toxicology knowledgebase, and then to generate profiles of test compounds, to compare with the classes in the knowledgebase, and thereby to predict toxic affects of the test substances. Another embodiment of the invention uses all the assays listed in FIG. 5 to produce a more extensive profile, and then uses a statistical method such as principle components analysis to identify the features with the highest predictive power for a selected profile of toxicology parameters.

In some profiles multiple cell types are identified and analyzed to more broadly indicate tissue associated responses. In addition, analyses can include combinations of assays where individual tissue cells are measured, along with higher throughput assays where the population of tissue cells or a region of a tissue section is analyzed as a whole for morphometry, texture, intensity, or other features, as will be appreciated by a person of skill in the art.

Figure 7:
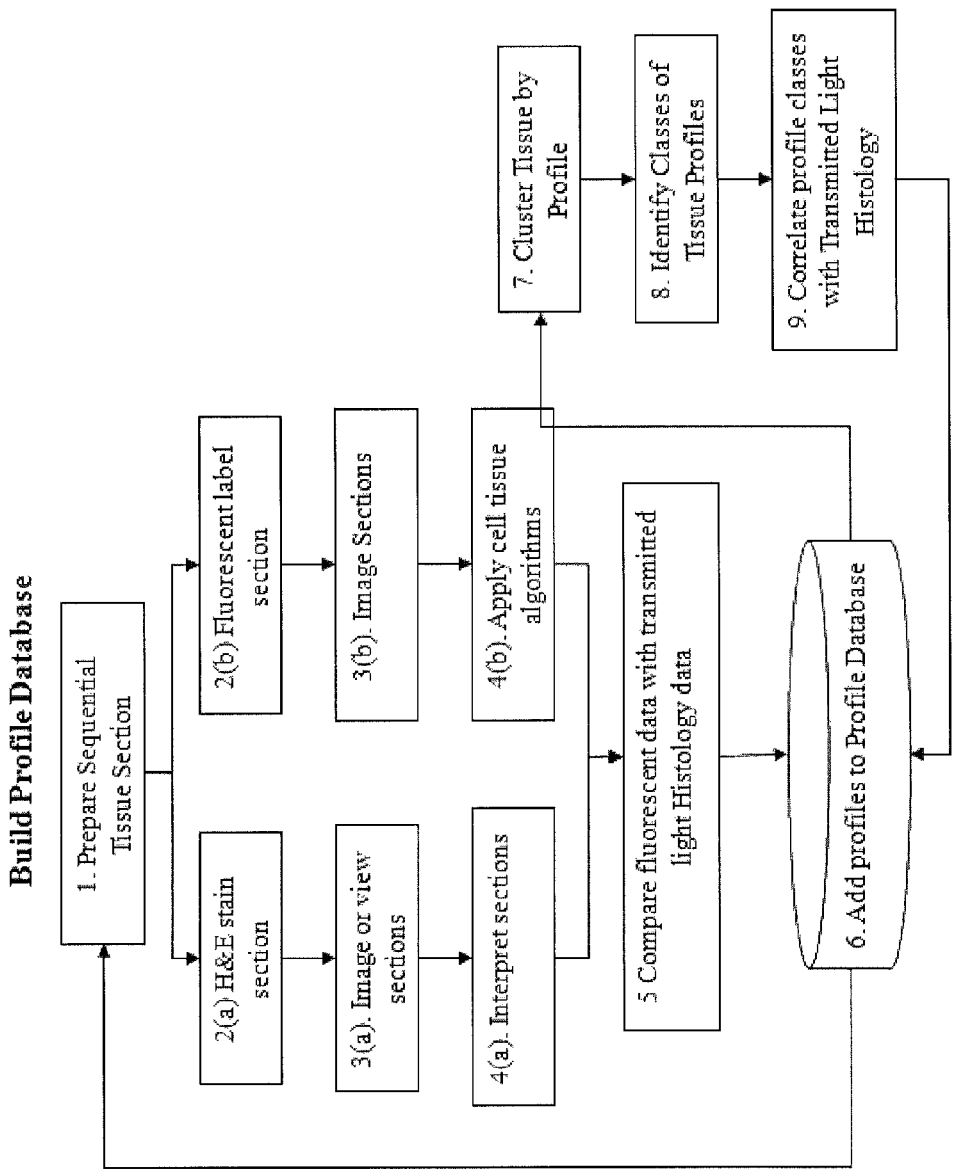
FIG. 7 is a schematic flow chart of the process of creating a reference profile database as described in one embodiment of the invention. Box 1: Sequential tissue sections are prepared and mounted. Box 2(a): One section is labeled with H&E stain for transmitted light imaging or review. Box 2(b): A second section is labeled with a panel of fluorescent labels to measure biomarkers. Boxes 3(a & b): Sections are imaged or viewed for interpretation. Boxes 4(a & b): Sections are analyzed and/or interpreted to create data. Box 5: Data from the sequential sections are compared and combined. Box 6: The cellular systems profile is added to database. Box 7: Tissue profiles in database are clustered to identify similarities. Box 8: Profile classes are identified. Box 9: Correlations between systems profiles and histological data are used to build a classifier which is stored in the database.
Figure 8:
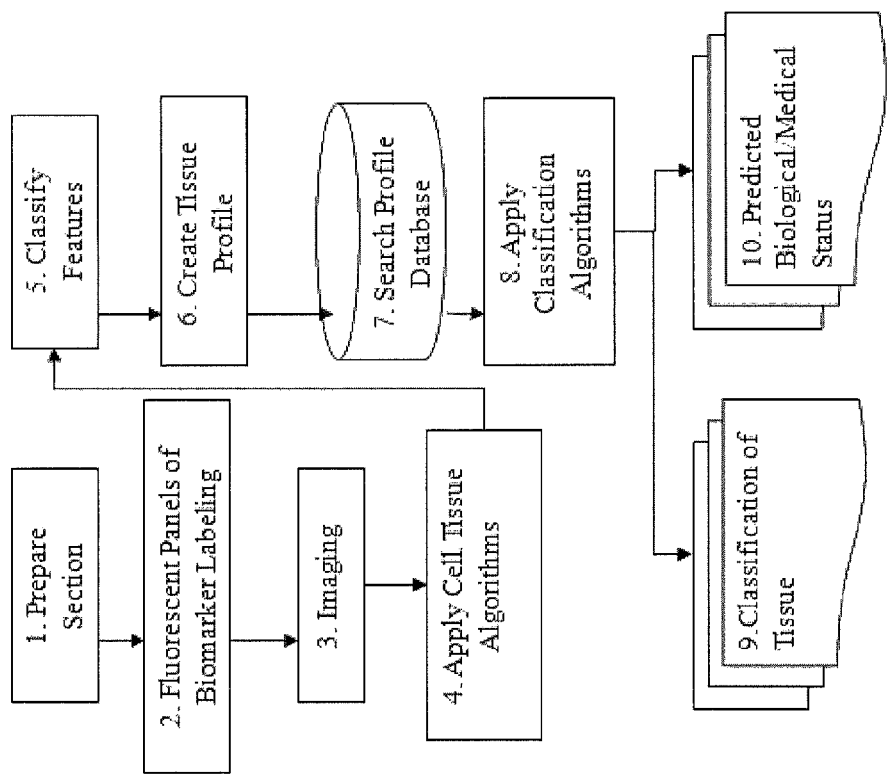
FIG. 8 is a flow chart illustrating the process of analyzing and classifying tissue, e.g., from a patient.
Figure 9:
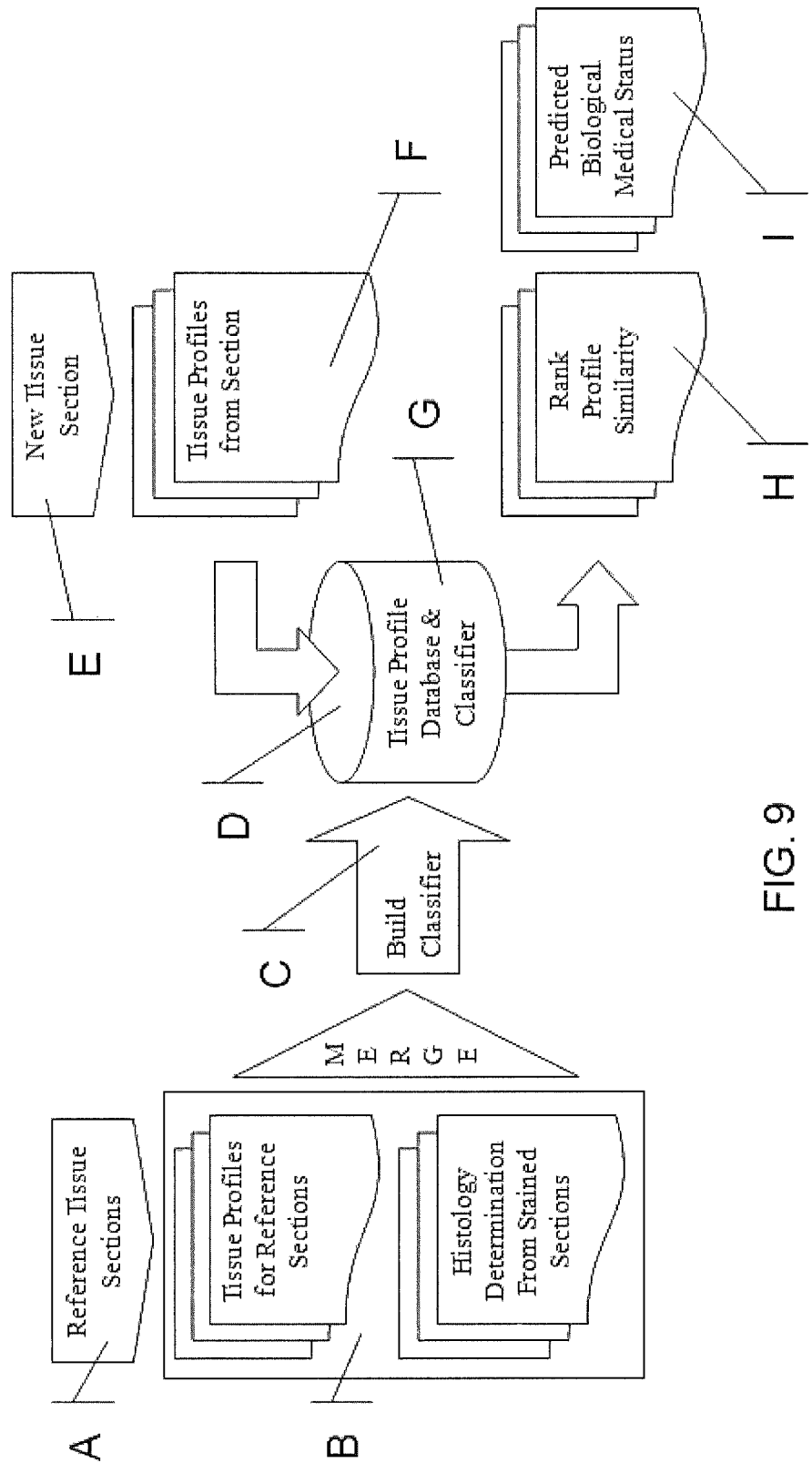
FIGS. 9A-I is a flow chart illustrating the overall process for automated tissue profiling in one embodiment of the invention.
Figure 10:
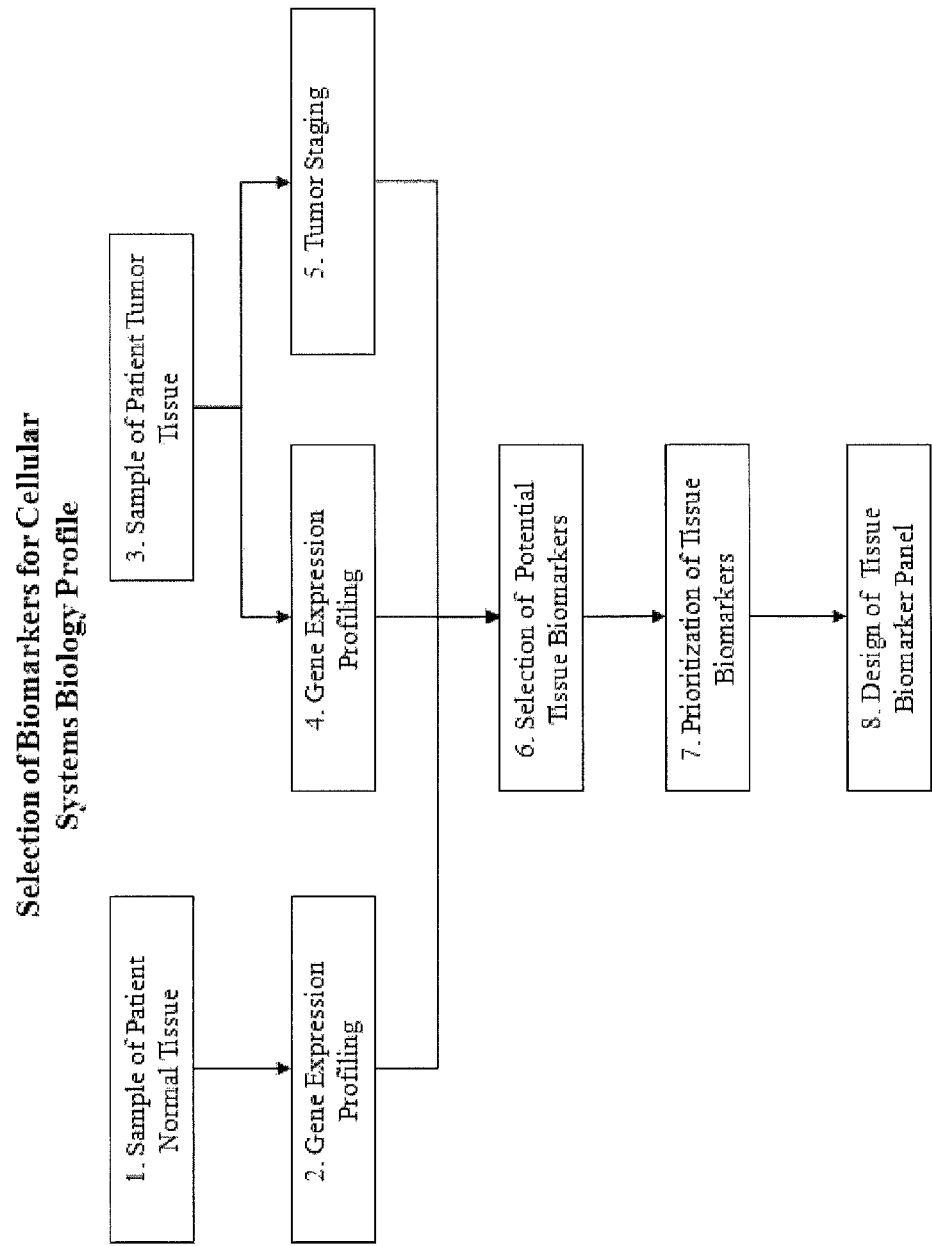
FIG. 10 is a flow chart of the process for selecting biomarkers for a cancer tissue profiling panel. Box (1) Normal tissue from Patient is (Box 2) analyzed by Gene Expression profiling. Box (3) A sample of tumor tissue from the same patient is (Box 4) analyzed by Gene Expression Profiling and is (Box 5) staged in the traditional manner. This combined information, comparing "normal" tissue with patient tumor tissue is (Box 6) used to identify potential biomarkers. Box (7) Gene products are prioritized based on known reference points including Her2/Neu and then antibodies acquired or produced to create test panels (Box 8). The design of the biomarker panel is based on the selection of combinations of cancer cell biomarkers that are multiplexed for fluorescence-based immunohistochemistry (IHC).

FIGS. 7 and 8 illustrate a flow diagram for two embodiments of the invention. The procedures in FIGS. 7 and 8 illustrate separate procedures. The procedure in FIG. 7 illustrates the procedure used to populate the tissue profile database and create the classes of response profiles linked to the histological determinations. The procedure in FIG. 8 illustrates the process for using the profile database to predict the classify tissue and identify medical states. The procedure in FIG. 8 comprises the following steps: 1. Tissue samples are prepared on slides or other carriers. 2. The tissues sections are fixed and stained with labels specific to the biomarker of interest. 3. The slides are read on an imaging system, such as an HCS reader, high throughput slide-scan reader, automated microscope or other detector. 4. Assay algorithms are applied to convert raw image data to assay data points. 5. The assay data points are clustered to produce response classes. 6. Responses classes are used to create a response profile for each of the classes. 7. Response profiles are established for the cells in control tissue specimens in each slide set. 8. Response profiles are clustered to identify unique profiles which can be used to classify and predict functional responses.

The procedure illustrated in FIG. 8 is used to evaluate substances for physiological effects. It comprises a sequence of steps: 1. Samples are prepared on slides or other carriers. 2. The cells are fixed and stained with labels specific to the biomarker of interest. 3. The plates are read on an imaging system, such as an HCS reader, high throughput slide-scan reader, automated microscope or other detector. 4. Assay algorithms are applied to convert raw image data to assay data points. 5. The tissue cell features are classified based on the assay data points. 6. The database is searched for physiological response profiles that match the cellular response profiles. 7. Predictions for physiological responses are made based on similarity of response profiles. 8. A report is generated tabulating the probability of each physiological response based on the substance response data.

FIG. 7 illustrates the overall sample flow while processing tissue sections to produce cellular systems biology profiles. A slide set comprises two or more tissue sections, each of which is used to collect a cellular systems biology profile. Each tissue section in the set produces an image set of images from one or more fields in each tissue section, at each of the wavelengths to be analyzed. Analysis of the image set produces a set of cellular systems biology features. The cellular systems biology features are processed and clustered to produce a cellular systems biology profiles to go into the data base, or to be used to search the data base to identify probable modes of physiological response or to set priorities for patient stratification.

Populations of cells within tissues can occupy discrete response classes, and move from class to class as a disease or treatment proceeds. In one example cellular systems biology profiles can be built through the application of Kolmogorov-Smirnov (KS) similarity analysis. KS values are one means to characterize a population and provide a measurement that can be used to cluster samples from many patients or other tissue sources. For example, cellular systems biology features based on KS values can be clustered by agglomerative clustering or other clustering methods, to build cellular systems biology profiles that identify tissues with similar cellular systems biology profiles. Other methods in addition to KS analysis can be used to process data prior to clustering, and a variety of clustering algorithms can be usefully applied.

FIG. 8 illustrates one embodiment of the invention, wherein the data flow is used to generate response profiles for a panel of tissue samples or tissue assays. Tissue samples from sources with known conditions or medical outcomes are processed to produce cellular response profiles, which are merged with other information on physiological conditions. The combined profiles of each tissue are clustered to identify unique profiles that can be used to distinguish classes of response. The response classes are stored in a database for use in classifying test samples. Test tissue samples are processed to produce cellular response profiles that are then matched to those in the database, and based on the similarity of the response to the database profiles, probabilities are calculated for each of the reference response profiles in the database, producing a similarity profile.

Algorithms: The algorithms, custom designed or encapsulated in the application software provided by HCS vendors, or other imaging software providers, produce multiple numerical feature values (cellular systems biology features) such as subcellular object intensities, shapes, and location for each cell within an optical field. The vHCS™ Discovery Toolbox (Cellomics, Inc), Metamorph (Molecular Devices), software from GE Healthcare and other HCS and image analysis packages can be used to batch analyze images following acquisition. Contingent on the type of tissue sample and its preparation, the total number of cells measured per sample is typically in the range of at least about 100 to at least about 10000, depending on the heterogeneity of the cellular response and the sensitivity of the assay. Examples of assay output parameters illustrate the function of application software. For example, to calculate changes in nuclear morphology, the average nuclear intensity value for each cell can be used. Nuclear condensation produces larger average nuclear intensity values while nuclear enlargement accompanied by DNA degradation produced smaller average nuclear intensity values relative to normal cells. The measurement of histone H3 phosphorylation is obtained using the average nuclear intensity of cells labeled with antibodies specific for phosphohistone H3 as previously reported. Those skilled in the art of imaging and cell analysis will recognize that there are many such algorithms readily available, and that there are many such cellular processes that are amenable to image-based analysis of cells and tissues to measure cellular/tissue functions.

Clustering and Classification of Responses: To quantify differences in the cellular systems biology feature responses induced in a population of tissue cells, such as healthy tissue, tumor tissue, and other abnormal tissues, several different methods can be effectively used. Within a population of similar cells or collections of cells in tissues, many different individual cellular response profiles are possible, including the well known heterogeneity in cellular responses [33, 34]. In one embodiment, the cellular systems biology feature response distribution for each cell parameter from a tissue section can be compared with that of a control sample using a KS goodness of fit analysis (KS value) [35]. The testing for significant changes in fluorescence-derived histograms is used to calculate KS values for replicate control samples and use these data to set a threshold (e.g., critical value), above which, a cellular systems biology feature response would be considered significant [36].

To perform significance testing of disease or therapy dependent changes or patient-specific differences in tissue features in multiplexed tissue-derived cell population distribution data, the one-dimensional KS test can be adapted to two dimensions as described by Peacock [37] and further refined by Fasano and Franceschini [38]. The two-dimensional cell population data distributions representing two physiological parameters from a cellular systems biology feature set are compared to the two-dimensional cell population data distributions obtained from multiple specimens. First, each distribution is divided into quadrants defined by the median x and y axis values calculated from the untreated cell data distributions. The two-dimensional KS value was then found by ranging through all four quadrants to find the maximal difference between the fraction of cells in each treated quadrant and the fraction of cells in each corresponding untreated quadrant.

The heterogeneity of cell populations within tissues can also be analyzed with other statistical methods to evaluate cellular systems biology profiles. In another embodiment of the invention, all the cell feature values from each cell are combined to create a cellular systems biology profile. The cellular systems biology profiles can consist of the actual measured values, and/or the principal components of the measured values, identified by standard methods [39, 40]. The cellular systems biology features from each population of tissue cells and from different samples are clustered using standard methods [39, 40], to produce cellular systems biology profiles. These profiles are used to build a classifier. All the cells in a single tissue sample, and therefore characteristic of the same medical condition, are classified into these response classes. The percent occupation of each of these classes then becomes a population response profile for that sample. In one example, the cellular systems biology profiles from the samples are linked to the cellular systems biology profiles (e.g., toxicity response profiles) from the reference samples and stored in the database. The cellular systems biology profiles from the test samples are classified using a probabilistic classifier based on the cellular systems biology profiles of the reference samples in the database to predict toxicological responses or to stratify patients. Other embodiments use alternative analysis algorithms or methods to cluster cell response profiles and create a classifier based on the known properties of a training set of tissue sections.

EXAMPLES

Example of tissue sample profiling of normal, diseased, and treated tissues in humans and animals using liver as a specific tissue example:

The liver, a gland comprised of a host of cell types, performs both exocrine and endocrine functions that are regulated by exquisitely orchestrated cellular activities. Furthermore, the liver is also responsible for the metabolism of drugs and steroids, many of which target their toxic activities to one or more cell types present in the liver. Other important functions of the liver include deiodination of triiodothyronine and thyroxine, gluconeogenesis and glycogenolysis, maintenance of normal glucose concentration in blood, etherification of free fatty acids into triglycerides, storage of glycogen, fat, and iron, detoxification of poisons and hydrogen peroxide, and hematopoiesis from the second to the eighth month of intrauterine life.

Thus, a cellular systems biology characterization of cells within the intact structure of the liver provides one of the most relevant profiles of normal or diseased tissue, and the effects that chemical compounds have on the liver as a living system.

The intact liver, like other glands, is comprised of a stroma and a highly vascularized and innervated parenchyma. Tissue sections of liver will therefore be comprised of several cell types including:

1. Squamous epithelial cells and fibroblasts—form part of the stroma
2. Nerve fibers—cellular processes that accompany blood vessels to innervate the parenchyma
3. Capillary endothelium—cells forming the walls of blood vessels
4. Kupfer cells—specialized macrophages
5. Fat cells—store triglycerides
6. Blood cells—cells that include erythrocytes, immune cells, and platelets
7. Hepatocytes—the most prevalent cell type in the liver. Hepatocytes perform most of the functions of the liver listed above.

Rationale for combining traditional transmitted light microscopy and multiplexed fluorescence based cytology of tumor sections: 1. Pathologists directly involved in test. 2. Allows direct comparison with present visual inspection of H&E stained sections as well as sections labeled with other manually detectable histochemical stains. 3. Maintains tissue organization and permits analysis of penetrating immune cells. 4. Allows implementation of automated imaging quantitation of the system. 5. Allows correlation of the presence and state of activation of the migratory immune cells with the presence and state of activation of the immune cells in the lymph nodes and peripheral blood. 6. Tissue toxicity profiles can be produced from either/or tissue-based profiles or peripheral blood profiles based on the tissue-based profile data. 7. The multiplexed, fluorescence-based biomarkers can be a combination of specific reagents to detect specific proteins and post-translational modifications of the proteins, specific RNA species including coding or non-coding RNA's, and micro-RNA's.

Below is a list of biomarkers that can be combined in various combinations to profile the systems response of liver tissue to disease or compound treatment:

1. Metabolism Biomarkers:
   Cytochrome P450 isotypes—expression levels and isotype ratios in hepatocytes.
   P-glycoprotein activity—expression level of a membrane-bound protein that pumps multiple compound substrates out of a cell, especially hepatocytes.
2. DNA Damage Biomarkers:
   Cell cycle regulation—The distribution of the total DNA content within the nucleus of a cell contained within a tissue slice can be determined using a nuclear label such as Hoechst 33342, Draq-5, or propidium iodide.
   Nuclear morphology and chromatin condensation—Nuclear damage can sometimes be correlated with a change in nuclear morphology or the condensation state of the chromatin. The morphology (e.g., shape and size) or the structure of the chromatin (brightness per unit area) of a nucleus contained within a tissue slice can be determined using a nuclear label such as Hoechst 33342, Draq-5, or propidium iodide.
   8-oxoguanine—Oxidative damage to DNA often generates an oxidized analog of guanine Increased 8-oxoguanine signals that the DNA in a cell has been damaged.
   Activation of DNA repair proteins (APE/ref-1)—The DNA in hepatocytes or any other cells present in liver that contain DNA are susceptible to damage due to disease or compound treatment. Changes in the expression level of APE/ref-1 signals that the DNA damage response mechanism has been activated within a cell.
   Histone H2A.X phosphorylation—The DNA in hepatocytes or any other cells present in liver that contain DNA are susceptible to damage due to disease or compound treatment. Phosphorylation of histone H2A.X signals that the DNA damage response mechanism has been activated within a cell.
   p53 protein activation.
   Rb protein phosphorylation
3. Cell Morphology and Differentiation Biomarkers:
   Cell spreading and hypertrophy
   Cell-cell or cell-stroma adhesion
   Angiogenesis of new vessels
   Remodeling of innervating nerve fibers
4. Stress-Induced Transcription Factor Activation or Inhibition Biomarkers:
   NF-κB
   ATF-2
   CREB
   AP-1
   MSK
   NFAT
   Stat1, 2, 3
   Oct-1
5. Changes in Phosphorylation State of Stress Kinases Biomarkers:
   ERK
   JNK
   p38
   RSK90
   MEK
6. Induction of Apoptosis or Necrosis Biomarkers:
   DNA content and degradation
   Nuclear morphology
   Caspase activation (multiple subtypes)
   Mitochondrial function (mass-potential)
   Bax mitochondrial translocation
   Cytochrome c mitochondrial release
   PARP activation
7. Remodeling of the Cytoskeleton Biomarkers:
   Actin cytoskeleton stability
   Microtubule cytoskeleton stability
8. Organelle Morphology Biomarkers:
   Mitochondrial size, number, and shape
   Golgi size and localization
   Peroxisome size and number
   Glycogen particle size and number
   Lysosome size and number
   Lipid droplet size and number
   Endoplasmic reticulum shape and localization
   Tight junction number and localization
9. Immune Cell Presence and Activity Biomarkers:
   The percentage and ratios of specific migratory immune cells in hepatocytes, lymph system, and blood supply.
   Phenotypes of key immune cell types in liver cancer tissues that reflect either an anti-tumor or tumor-supporting function.
   Apoptosis of immune cells
   Expression of death receptor ligands such as TRAIL
   Expression of biomarkers associated with immune cell dysfunction such as PD1 in lymphocytes
   NK and LAK cell activity to characterize anti-tumor surveillance Example of tissue preparation: In one embodiment, a small animal such as a mouse or a rat is treated with one or more test compounds for various lengths of time (1 min to 21 d). In another embodiment, a small animal model of disease including metabolic models such as diabetes, cancer, or other models that either directly or indirectly involve the liver will be used. In yet another embodiment, human liver tissue from diseased or compound treated patients will be used. Normal, diseased, and treated tissue samples will be prepared. Tissue samples will be processed as either frozen sections or formaldehyde fixed paraffin-embedded sections. In addition, tissue samples will also be obtained for gene expression analysis.

For clarity, other major tissue types will be treated the same way. Panels of biomarkers of both a general cell responses and responses more tissue-specific will be produced and applied.

The optimal combination (multiplexing) of the liver tissue biomarkers, will be the key to creating an optimal cellular systems biology profile of the tissue. The optimal number of number of multiplexed biomarkers will range from about four to about twelve biomarkers. Normal, diseased, and treated tissue samples will be prepared. Tissue samples will be processed as either frozen sections or formaldehyde fixed paraffin-embedded sections. In addition, tissue samples will also be obtained for gene expression analysis.

1. Below is an Example of Liver Tissue Analysis:
   a. Gene expression profiling is performed that compares "normal" liver tissue with tissues from diseased or compound treated animals.

b. Gene expression informatics—Gene expression profiles analyzed by informatics tools to characterize gene expression as a function of disease or compound treatment to identify gene products.

c. Gene products prioritized based on known reference points from normal liver tissue and then antibodies acquired or produced to create test panels.

2. Combinations of Histological Stains and Key Biomarkers Multiplexed for Fluorescence-Based Immunocytochemistry of the "Functional Biomarkers":

a. Multiple 5 μm sections prepared from liver tissue. The first section labeled with H&E or other histological stain for traditional pathological analysis. The successive sections processed for multiplexed, fluorescence-based cytometry.

b. In addition to the panels of potential biomarkers based on the gene expression profiling, some sections will be labeled with multiplexed panels of antibodies to key migratory immune cells; including lymphocytes (e.g. CD3 and CD8). The level of immune cell activation, concentration and organization will be an important element of the profile.

Example biomarker combinations to profile liver tissues: In one embodiment, liver tissue slices are labeled for two or more biomarkers to profile differences between non-diseased and diseased or non-treated and treated animals. Biomarkers of a wide range of tissue functions are preferable since they provide breadth to the systems profile of the tissue. The number of biomarkers in one embodiment is about four to about ten biomarkers, and multiple biomarkers can be labeled in the same tissue section. This permits the comparison of some biomarker activities within the same cells.

In one example, a rat is treated with an apoptosis-inducing compound such as paclitaxel or camptothecin for times ranging from about 30 min to about 21 d using multiple doses in the range from about 1 μg/kg up to about 100 mg/kg. After treatment, the animal is sacrificed and the liver tissue either frozen and sectioned or fixed with a chemical such as formaldehyde and then impregnated with paraffin using standard methods before sectioning. A hematoxylin and eosin (H&E) stain can then be performed on one or more sections to provide a sample for traditional, transmitted light-based pathology interpretation. Other sequential sections can be labeled with combinations of fluorescent immunoreagents and physiological indicator dyes for image-based analysis, for example:

Sequential Section #1
    1. Hoechst 33342 to label the nuclei and provide measurements of nuclear morphology, cell cycle regulation, and chromatin condensation.
    2. Anti-phospho-histone H2A.X as a biomarker of oxidative DNA damage
    3. Anti-p53 as a biomarker of the DNA damage response.
    4. Anti-phospho-c-jun as a biomarker of stress kinase induction.

Sequential section #2
    1. Hoechst 33342
    2. Anti-cytochrome c as a biomarker of mitochondrial number, size and shape.
    3. Anti-alpha-tubulin as a biomarker of microtubule cytoskeletal remodeling.
    4. Fluorescently labeled phalloidin as a biomarker of actin cytoskeletal remodeling.

Sequential Section #3
    1. Hoechst 33342
    2. Anti-phospho-retinoblastoma protein as a biomarker of cell cycle checkpoint activity.
    3. Anti-NF-kappa-B as a biomarker of inflammation-related cell signaling.
    4. Anti-CD3 as a biomarker of lymphocyte infiltration into the tissue.

Sequential Section #4
    1. Hoechst 33342
    2. Anti-activated-caspase 3 as a biomarker of apoptosis.
    3. Anti-PMP70 as a biomarker of peroxisome size and number.
    4. Anti-cytochrome P450 as a biomarker of hepatocyte metabolic activity.

Example of Patient Sample Profiling for Breast Cancer: Cancer is a systems biology disease that requires a systems biology approach to create better stratification of individual patients for better diagnostics and treatments. Cancer is also an inflammatory process that involves the full range of the immune response. Therefore, tumors contain a combination of cancer cells at different stages of evolution, normal cells and an infiltration of the migratory immune cells such as dendritic cells, macrophages and lymphocytes. Tumor "cellular systems biology" characterization should therefore be a combination of tumor cell biomarkers and immune cell biomarkers. A key to tumor cellular systems biology is the use of a multiplexed panel of tumor biomarkers for cancer cells and immune cells that will better stratify patients. In addition, correlations with lymph nodes and peripheral blood cell analysis would determine if circulating immune cells carry tumor specific information that could create a very simple blood cell test. The number, type and level of activation of migratory immune cells in the blood could also become a "window" on the tumor itself.

Rationale For Combining Traditional Transmitted Light Microscopy and Multiplexed Fluorescence-Based Cytology of Tumor Sections: 1. Pathologists directly involved in test. 2. Allows direct correlation with present visual inspection of H&E stained sections and staging tumors by morphometric analyses. 3. Builds on the success of Her2/Neu as a single "functional protein" biomarker, but which also only identifies a small sub-set of patients. 4. Maintains tissue organization and permits analysis of penetrating immune cells. 5. Enables the development of a "systems" profile of the tumor including multiplexed breast cancer biomarkers and migratory immune cell presence and state of activation. 6. Allows implementation of automated imaging quantitation of the system. 7. Allows correlation of the presence and state of activation of the migratory immune cells with the presence and state of activation of the immune cells in the lymph nodes and peripheral blood. 8. Stratification and diagnostic tests can be produced from either/or tissue-based profiles or peripheral blood profiles based on the tissue-based profile data. 9. The multiplexed, fluorescence-based biomarkers can be a combination of specific reagents to detect specific proteins and post-translational modifications of the proteins, specific RNA species, including micro-RNA's either coding or non-coding in cells.

Measurement of specific protein expression and state of activation, as well as the presence of specific micro RNA's within cells and tissues are key "functional" read-outs. The expression of a gene is only one element of the systems biology and the present genomic tests are only correlations of gene expression without any functional information. Cellular functions are carried out primarily by proteins whose expression level, cellular localization and post-translational modification are responsible for carrying out normal and abnormal functions. Specific microRNA's have also been shown to be disease specific and are critical in regulating gene expression, similar to regulatory proteins. In addition, tumors are systems in that they are a complex integration of normal cells, a range of genetically evolving cancer cells and migrating immune cells. Therefore, a cellular systems biology profile of multiple protein and/or micro RNA biomarkers is important.

Background on the Importance of the Immune System in Breast Cancer: The immune system becomes dysfunctional early in the process of cancer occurrence and continues throughout the evolution of the cancer stages leading to metastatic disease. The migratory immune cells are attracted to the growing tumors by pro-inflammatory cytokines and chemotactic factors. Tumor infiltrating lymphocytes release growth factors and cytokines that actually promote growth of the tumors, while the anti-tumor functions are weak or non-existent. Dendritic cells and tumor-associated macrophages present in the tumor exhibit phenotypes that demonstrate a supporting role for tumor growth. Regulatory T cells accumulate in the tumors, as well as in the tumor-draining lymph nodes and peripheral blood of patients. These latter cells actually protect tumor cells as part of the "recognition of self" immune process. Therefore, the immune system is mostly a tumor-promoting system and supports the progression and metastasis in most cancers.

Gene expression fingerprints from tumor samples have been used to distinguish subtypes of breast cancers and to assign some prognostic index. These gene expression profiles usually identify genetic profile "signatures" indicative of the infiltration of the migratory immune cells. Unfortunately, in methods such as gene expression profiling, the disaggregated tumor samples the "tumor as a system" is lost since the whole tissue architecture and tumor cell-migratory immune cell structural relationships are lost.

Tissue sections, including tissue micro-arrays (TMA's) used in patient stratification and diagnostic tests are valuable, since the tumor "system" can be analyzed and quantified through the integrated use of traditional transmitted light stains that are standard in pathology and oncology with multiplexed fluorescence-based biomarkers of more functional parameters of both the migratory immune cells and the cancer cells. Therefore, the traditional information from pathology can be combined with panels of biomarkers using multiplexed fluorescence.

In addition to the primary tumors, the tumor-draining and non-sentinel lymph nodes are important sites of tumor and immune system interactions that could aid in the "functional cellular systems biology signature". For example, the presence of tumor cells in the tumor-draining lymph nodes affects the types and numbers of immune cells within the nodes. Furthermore, the non-sentinel auxiliary nodes can also be influenced by local tumor growth, since it has been shown that CD4 T cells and dendritic cell counts have been used to predict survival in breast cancer patients. Also, it is clear that tumor progression also can be observed in the peripheral immune system by analysis of the circulating leukocytes, circulating T cells and other immune cells. Therefore, a correlative analysis of the patient's circulating immune cells in the peripheral blood with the tumor "system", as well as lymph node "system" will create the an excellent opportunity to create powerful tests in tumors, lymph nodes and blood.

Below is a list of biomarkers that can be combined in various combinations for optimal staging and diagnostic for breast cancer (in one embodiment, the combination of cancer cell and immune biomarkers may be most suitable):

Examples of Cancer Cell Biomarkers:
Her2/Neu Protein (now used as single biomarker)
Estrogen Receptor Protein (ER)
Ki-67
Cox-2
P16

A growing number of key proteins or post-translational modifications of proteins correlated with a cancer process A growing number of micro RNA's correlated with specific cancers Examples of Immune Biomarkers:

The percentage and ratios of specific migratory immune cells in tumors, tumor draining lymph nodes, non-sentinel lymph nodes and peripheral blood Phenotypes of key immune cell types in breast cancer patients that reflect either an anti-tumor or tumor-supporting function Apoptosis of immune cells Expression of death receptor ligands such as TRAIL Expression of biomarkers associated with immune cell dysfunction such as PD1 in Tumor Infiltrating Lymphocytes.

NK and LAK cell activity to characterize anti-tumor surveillance

The optimal combination (also referred to herein as multiplexing) of the cancer cell and immune biomarkers, especially in the tumors, will be the determinative to creating an optimal cellular systems biology profile of the patient. In one embodiment, the optimal number of number of multiplexed biomarkers is in the range from about four to about twelve biomarkers.

Technical Steps: Normal and breast cancer positive patient materials will be prepared. Patient tumor samples will be processed as either frozen sections or formaldehyde fixed paraffin-embedded sections. Furthermore, lymph node samples will be treated the same as the primary tumors. In addition, samples will be obtained from the tumors for gene expression analysis. Migratory immune cells will also be separated from the blood samples for both flow cytometry and image cytometry. Below is an outline of steps in one method of the invention:

1. Patient Tumor Sample-Gene Expression Profiling comparing "normal" tissue with patient tumors staged in the traditional manner.

2. Gene Expression Informatics-Gene Expression Profiles analyzed by informatics tools to characterize gene expression as a function of stage of breast cancer and to identify gene products (use Her2/Neu as reference).

3. Gene products prioritized based on known reference points including Her2/Neu and then antibodies acquired or produced to create test panels.

4. Combinations of selected cancer cell biomarkers multiplexed for fluorescence-based immunohistochemistry.

5. Multiple 5 micron tissue sections prepared from tumor samples. The first section labeled for H&E for traditional staging by a pathologist. The successive sections processed for multiplexed, fluorescence-based cytometry.

6. In addition to the panels of potential cancer cell biomarkers based on the gene expression profiling, some sections will be labeled with multiplexed panels of antibodies to key migratory immune cells; including lymphocytes (e.g., CD3 and/or CD8). The level of immune cell activation, concentration and organization will be an important element of the profile.

The percentage and ratios of specific migratory immune cells in tumors, tumor draining lymph nodes, non-sentinel lymph nodes and peripheral blood will be calculated and used build cellular systems biology profiles. Example percentage ranges of immune cells in tissues are as follows:

Lymphocytes: 1%-90% (distinct sub-types within this percentage)
Neutrophils: 1%-90%
Eosinophils: 0.01%-50%

Monocytes: 0.01%-50% (distinct sub-types within this percentage)

Example ranges of ratios of immune cells in tissues for cellular systems biology profiling:

T-cell lymphocyte subtype I/T-cell lymphocyte subtype II: 0.01-1000

T-cell lymphocytes/B-cell lymphocytes: 0.1-1000

Dendritic cells/lymphocytes: 0.01-1000

Macrophages/lymphocytes: 0.01-1000

Lymphocyte sub-set/lymphocyte sub-set: 0.01-1000

The optimal combination of biomarkers that suitably stratify patient samples from stage I to stage IV will be selected for profiling on new patients. New patients will allow the direct correlation of peripheral immune cells with the tumor tissue and lymph node sections.

Example of Profiling Brain Tissue for Biomarkers of Alzheimer's Disease:

In this embodiment, human brain tissue is obtained, fixed, and sectioned. A subset of sections are labeled with one or more stains to visualize morphological structures within the tissue associated with the pathology of Alzheimer's disease. In one example, a silver-based stain is used to visualize hallmarks of Alzheimer's disease such as neurite plaques and neurons with neurofibrillary tangles [41]. Analysis of the silver-stained tissue from multiple patients before, during, or after treatments with drugs provides data which are then entered into a profile.

In a second embodiment, another subset of the same tissue sections from the same patient is reacted with reagents to label two or more biomarkers in either the same tissue section or in contiguous serial sections from the same tissue sample. Example biomarkers that can be labeled using immunofluorescence approaches include Aβ42, Aβ40, von Willebrand factor, and the microtubule binding protein tau [42]. Other biomarkers are also possible. These include phosphorylated APP (amyloid precursor protein) and unphosphorylated APP. Furthermore, biomarkers of other cellular processes can be included in the profile. Profiles built from multiple biomarker labels measured within tissues from a single patient or profiles built from biomarker labels measured in multiple patient tissue samples are clustered to identify unique profiles that can be used to classify and predict possible patient outcomes, or functional responses to drug treatments, or a combination of both.

REFERENCES

1. Hood, L. and R. M. Perlmutter, The impact of systems approaches on biological problems in drug discovery. Nat Biotechnol, 2004. 22(10): p. 1215-7.
2. Hood, L., et al., Systems biology and new technologies enable predictive and preventative medicine. Science, 2004. 306(5696): p. 640-3.
3. Taylor, D. L., et al., Potential of machine-vision light microscopy in toxicologic pathology. Toxicol Pathol, 1994. 22(2): p. 145-59.
4. Schroeder, K. S. and B. D. Neagle, FLIPR: A New Instrument for Accurate, High Throughput Optical Screening. J Biomol Screen, 1996. 1(2): p. 75-80.
5. Giuliano, K. A., et al., High-Content Screening: A New Approach to Easing Key Bottlenecks in the Drug Discovery Process. J Biomol Screen, 1997. 2(4): p. 249-259.
6. Dow, A., S. A. Shafer, and A. S. Waggoner. Morphological segmentation of multiprobe fluorescence images for immunophenotyping in melanoma tissue sections. in Intelligent Robots and Computer Vision XII: Algorithms and Techniques. 1993: SPIE.
7. Dow, A. I., et al., Automatic multiparameter fluorescence imaging for determining lymphocyte phenotype and activation status in melanoma tissue sections. Cytometry, 1996. 25(1): p. 71-81.
8. Galbraith, W., et al., Imaging cytometry by multiparameter fluorescence. Cytometry, 1991. 12(7): p. 579-96.
9. Camp, R. L., G. G. Chung, and D. L. Rimm, Automated subcellular localization and quantification of protein expression in tissue microarrays. Nat Med, 2002. 8(11): p. 1323.
10. Taylor, D. and K. Giuliano, Mutiplexed high content screening assays create a cellular systems biology approach to drug discovery. Drug Discov Today, 2005. 2(2): p. 149-154.
11. Xu, J. J., D. Diaz, and P. J. O'Brien, Applications of cytotoxicity assays and pre-lethal mechanistic assays for assessment of human hepatotoxicity potential. Chem Biol Interact, 2004. 150(1): p. 115-28.
12. Perlman, Z. E., T. J. Mitchison, and T. U. Mayer, High-Content Screening and Profiling of Drug Activity in an Automated Centrosome-Duplication Assay. Chembiochem, 2005. 6(2): p. 218.
13. Lee, K. M., J. H. Kim, and D. Kang, Design issues in toxicogenomics using DNA microarray experiment. Toxicol Appl Pharmacol, 2005.
14. Abraham, V. C., D. L. Taylor, and J. R. Haskins, High content screening applied to large-scale cell biology. Trends Biotechnol, 2004. 22(1): p. 15-22.
15. Giuliano, K. A., J. R. Haskins, and D. L. Taylor, Advances in high content screening for drug discovery. Assay Drug Dev Technol, 2003. 1(4): p. 565-77.
16. Conway, B. R. and K. T. Demarest, The use of biosensors to study GPCR function: applications for high-content screening. Receptors Channels, 2002. 8(5-6): p. 331-41.
17. Woollacott, A. J. and P. B. Simpson, High Throughput Fluorescence Assays for the Measurement of Mitochondrial Activity in Intact Human Neuroblastoma Cells. J Biomol Screen, 2001. 6(6): p. 413-420.
18. Lovborg, H., P. Nygren, and R. Larsson, Multiparametric evaluation of apoptosis: effects of standard cytotoxic agents and the cyanoguanidine CHS 828. Mol Cancer Ther, 2004. 3(5): p. 521-6.
19. Tencza, S. B. and M. A. Sipe, Detection and classification of threat agents via high-content assays of mammalian cells. J Appl Toxicol, 2004. 24(5): p. 371-7.
20. Waggoner, A., Fluorescence probes for analysis of cell structure, function and health by flow and imaging cytometry., in Applications of Fluorescence in the Biomedical Sciences, D. Taylor, et al., Editors. 1986, Alan R. Liss, Inc.: New York. p. 3-28.
21. Chalfie, M., et al., Green fluorescent protein as a marker for gene expression. Science, 1994. 263(5148): p. 802-5.
22. Chudakov, D. M., S. Lukyanov, and K. A. Lukyanov, Fluorescent proteins as a toolkit for in vivo imaging. Trends Biotechnol, 2005. 23(12): p. 605-13.
23. Umezawa, Y., Genetically encoded optical probes for imaging cellular signaling pathways. Biosens Bioelectron, 2005. 20(12): p. 2504-11.
24. Giuliano, K. A. and D. L. Taylor, Fluorescent-protein biosensors: new tools for drug discovery. Trends Biotechnol, 1998. 16(3): p. 135-40.
25. Giuliano, K. A. and D. L. Taylor, Measurement and manipulation of cytoskeletal dynamics in living cells. Curr Opin Cell Biol, 1995. 7(1): p. 4-12.
26. Zhang, S., C. Ma, and M. Chalfie, Combinatorial marking of cells and organelles with reconstituted fluorescent proteins. Cell, 2004. 119(1): p. 137-44.

27. Michalet, X., et al., Quantum dots for live cells, in vivo imaging, and diagnostics. Science, 2005. 307(5709): p. 538-44.

28. Hemmila, I. and V. Laitala, Progress in lanthanides as luminescent probes. J Fluoresc, 2005. 15(4): p. 529-42.

29. Roda, A., et al., Biotechnological applications of bioluminescence and chemiluminescence. Trends Biotechnol, 2004. 22(6): p. 295-303.

30. Mitchison, T. J., Small-molecule screening and profiling by using automated microscopy. Chembiochem, 2005. 6(1): p. 33-9.

31. Perlman, Z. E., et al., Multidimensional drug profiling by automated microscopy. Science, 2004. 306(5699): p. 1194-8.

32. Abraham, V. C., et al., Automated Classification of Individual Cellular Responses Across Multiple Targets. Preclinica, 2004. 2(5): p. 349-355.

33. Rubin, H., Early origin and pervasiveness of cellular heterogeneity in some malignant transformations. Proc Natl Acad Sci USA, 1984. 81(16): p. 5121-5.

34. Elsasser, W. M., Outline of a theory of cellular heterogeneity. Proc Natl Acad Sci USA, 1984. 81(16): p. 5126-9.

35. Giuliano, K. A., et al., Systems cell biology knowledge created from high content screening. Assay Drug Dev Technol, 2005. 3(5): p. 501-14.

36. Giuliano, K. A., Y.-T. Chen, and D. L. Taylor, High-Content Screening with siRNA Optimizes a Cell Biological Approach to Drug Discovery: Defining the Role of P53 Activation in the Cellular Response to Anticancer Drugs. J Biomol Screen, 2004. 9(7): p. 557-568.

37. Peacock, J. A., Two-dimensional goodness-of-fit testing in astronomy. Monthly Notices of the Royal Astronomical Society, 1983. 202: p. 615-627.

38. Fasano, G. and A. Franceschini, A multidimensional version of the Kolmogorov-Smirnov test. Monthly Notices of the Royal Astronomical Society, 1987. 225: p. 155-170.

39. Witten, I. H. and E. Frank, Data Mining: Practical Machine Learning Tools and Techniques. Second ed. Morgan Kaufmann Series in Data Management Systems, ed. J. Gray. 2005, San Francisco, Calif.: Elsevier. 523.

40. Venables, W. N., B. D. Ripley, and W. N. Venables, Modern applied statistics with S. 4th ed. Statistics and computing. 2002, New York: Springer. xi, 495 p.

41. Switzer, R. C., III, S. K. Campbell, and L. Murdock, Histological analysis method. 1993: USA.

42. Uchihara, T., et al., Triple immunofluorolabeling with two rabbit polyclonal antibodies and a mouse monoclonal antibody allowing three-dimensional analysis of cotton wool plaques in Alzheimer disease. J Histochem Cytochem, 2003. 51(9): p. 1201-6.

43. Strategic analysis of the ADME/Tox technologies market in Europe. 2005, Frost and Sullivan.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of producing a cellular systems biology profile that characterizes the medical state of one or more isolated tissue samples, the method comprising:

a) labeling at least one section from one or more isolated tissue samples with a histological stain, thereby producing a histologically stained section;
b) labeling at least one other section from the one or more isolated tissue samples with a panel of fluorescently labeled reagents, thereby producing a fluorescently labeled section, wherein each fluorescently labeled reagent is specific for a biomarker, and wherein the panel of fluorescently labeled reagents detects at least four different biomarkers, and wherein the detection of a biomarker is a read-out of one or more features of a cellular systems biology profile;
c) imaging the histologically stained section with at least a first optical mode, wherein the imaging produces a first set of data;
d) imaging the fluorescently labeled section with at least a second optical mode, wherein the imaging produces a second set of data;
e) analyzing the first set of data and the second set of data to identify five or more features, wherein at least one feature is identified in each of the first set of data and the second set of data; and
f) calculating the interrelationships of the five or more features, wherein the interrelationships of the five or more features generates a cellular systems biology profile that characterizes the medical state of the one or more isolated tissue samples, wherein at least the steps of d) to f) are automated;
thereby providing a method of producing a cellular systems biology profile that characterizes the medical state of the one or more isolated tissue samples.

2. The method of claim 1, wherein the panel of fluorescently labeled reagents is selected from the group consisting of fluorescently labeled antibodies, fluorescently labeled peptides, fluorescently labeled proteins, fluorescently labeled aptamers, fluorescently labeled oligonucleotides, fluorescently labeled chemicals, fluorescent chemicals, and a combination thereof.

3. The method of claim 1, wherein at least one biomarker is a nucleic acid biomarker.

4. The method of claim 1, wherein the medical state of the one or more isolated tissue samples is the presence or absence of a disease, the presence or absence of a cancer and/or the presence or absence of toxicity.

5. The method of claim 4, wherein the tissue is liver.

6. The method of claim 5, wherein the panel of fluorescently labeled reagents comprises:

a) a set of fluorescently labeled reagents specific for at least four hepatocyte biomarkers;
b) a set of fluorescently labeled reagents specific for at least four stromal cell biomarkers;
c) a combination of:
  i) a set of fluorescently labeled reagents specific for at least three hepatocyte cell biomarkers; and
  ii) a set of fluorescently labeled reagents specific for at least three stromal cell biomarkers;
or
d) a combination thereof.

7. The method of claim 6, wherein the panel of fluorescently labeled reagents detects biomarkers selected from the group consisting of metabolism biomarkers, DNA damage biomarkers, cell morphology and differentiation biomarkers, stress-induced transcription factor activation or inhibition biomarkers, activation state of stress kinase biomarkers, apoptosis and necrosis biomarkers, cytoskeletal remodeling biomarkers, organelle morphology biomarkers, and a combination thereof.

8. The method of claim 6, wherein the panel of fluorescently labeled reagents detects biomarkers selected from the group consisting of stress-induced transcription factor activation or inhibition biomarkers, immune cell presence and activity biomarkers, cell-cell or cell-stroma adhesion biomarkers, angiogenesis biomarkers, immune cell apoptosis biomarkers, and a combination thereof.

9. The method of claim 6, wherein the panel of fluorescently labeled reagents detects biomarkers selected from the group consisting of cytochrome P450 isotypes, P-glycoprotein, 8-oxoguanine, APE/ref-1, H2A.X phosphorylation, p53, Rb phosphorylation, ERK, JNK, p38, RSK90, MEK, NF-kappaB, COX-2, ATF-2, CREB, AP-1, MSK, NFAT, Stat1, 2, 3, Oct-1 and nuclear morphology biomarkers.

10. The method of claim 6, wherein the panel of fluorescently labeled reagents detects biomarkers selected from the group consisting of macrophage biomarkers, dendritic cell biomarkers, fibroblast biomarkers, NK cell biomarkers, LAK cell biomarkers, TRAIL, PD1, COX-2, NF-kappaB, CD8, CD3 and immune cell apoptosis biomarkers.

11. The method of claim 1, wherein at least one interrelationship of the five or more features is a ratio of the one or more features.

12. The method of claim 1, wherein the medical state is cancer, and wherein the panel of fluorescently labeled reagents comprises:
  a) a set of fluorescently labeled reagents specific for at least four cancer cell biomarkers;
  b) a set of fluorescently labeled reagents specific for at least four migratory immune cell biomarkers;
  c) a combination of:
    i) a set of fluorescently labeled reagents specific for at least three cancer cell biomarkers; and
    ii) a set of fluorescently labeled reagents specific for at three migratory immune cell biomarkers;
  or
  d) a combination thereof.

13. The method of claim 12, wherein the cancer is breast cancer.

14. The method of claim 12, wherein the migratory immune cell biomarkers comprise one or more biomarkers for macrophage cells, dendritic cells and/or regulatory T cells.

15. The method of claim 12, wherein the panel of fluorescently labeled reagents further comprises one or more fluorescently labeled reagents specific for a non-cancerous cell.

16. The method of claim 15, wherein the non-cancerous cell comprises a cell selected from the group consisting of fibroblasts, epithelial cells, endothelial cells and nerve cells.

17. The method of claim 1, further comprising producing a cellular systems biology profile of at least one isolated peripheral blood sample obtained from the same source as the one or more tissue samples, comprising:
  a) labeling at least one blood sample smear from the isolated peripheral blood sample obtained from the same source as the one or more tissue samples with a panel of fluorescently labeled reagents, thereby producing a fluorescently labeled blood sample smear, wherein each fluorescently labeled reagent is specific for a biomarker, and wherein the panel of fluorescently labeled reagents detects at least four different biomarkers, and wherein the detection of a biomarker is a read-out of one or more features of a cellular systems biology profile;
  b) imaging the fluorescently labeled blood sample smear with at least a third optical mode, wherein the imaging produces a third set of data;
  c) analyzing the third set of data to identify five or more features; and
  d) calculating the interrelationships of the five or more features, wherein the interrelationships of the five or more features generates a cellular systems biology profile wherein the interrelationships of the five or more features generates a cellular systems biology profile of the at least one blood sample smear,
thereby producing a cellular systems biology profile of the at least one isolated peripheral blood sample obtained from the same source as the one or more tissue samples.

* * * * *

UNITED STATES PATENT AND TRADEMARK OFFICE
CERTIFICATE OF CORRECTION

| | | |
|---|---|---|
| PATENT NO. | : 8,597,899 B2 | Page 1 of 1 |
| APPLICATION NO. | : 13/593663 | |
| DATED | : December 3, 2013 | |
| INVENTOR(S) | : Albert H. Gough, Kenneth A. Giuliano and D. Lansing Taylor | |

It is certified that error appears in the above-identified patent and that said Letters Patent is hereby corrected as shown below:

Title Page: in the Related U.S. Application Data item (63), Line 3, delete "as" and insert
--April 14, 2009, which is the U.S. National Stage of International--

Title Page: in the Related U.S. Application Data item (63), Line 4, delete "on" and insert --filed--

Signed and Sealed this
Twenty-fifth Day of February, 2014

Michelle K. Lee
*Deputy Director of the United States Patent and Trademark Office*